(12) United States Patent
Buschmann et al.

(10) Patent No.: US 9,914,705 B2
(45) Date of Patent: *Mar. 13, 2018

(54) 1-ARYL-3-AMINOALKOXY PYRAZOLES AS SIGMA LIGANDS ENHANCING ANALGESIC EFFECT OF OPIOIDS AND ATTENUATING THE DEPENDENCY THEREOF

(71) Applicant: LABORATORIOS DEL DR. ESTEVE, S.A., Barcelona (ES)

(72) Inventors: Helmut Heinrich Buschmann, Aachen (DE); Jose Miguel Vela-Hernandez, Barcelona (ES); Daniel Zamanillo-Castanedo, Barcelona (ES)

(73) Assignee: LABORATORIOS DEL DR. ESTEVE, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/502,422

(22) Filed: Sep. 30, 2014

(65) Prior Publication Data

US 2015/0018354 A1   Jan. 15, 2015

Related U.S. Application Data

(63) Continuation of application No. 12/988,951, filed as application No. PCT/EP2009/054974 on Apr. 24, 2009, now Pat. No. 8,877,753.

(30) Foreign Application Priority Data

Apr. 25, 2008  (EP) .................... 08380122

(51) Int. Cl.
| | |
|---|---|
| *A61K 31/4152* | (2006.01) |
| *A61K 31/4155* | (2006.01) |
| *A61K 31/485* | (2006.01) |
| *A61K 31/5377* | (2006.01) |
| *C07D 231/22* | (2006.01) |
| *C07D 401/12* | (2006.01) |
| *C07D 403/12* | (2006.01) |
| *C07D 471/04* | (2006.01) |
| *A61K 45/06* | (2006.01) |

(52) U.S. Cl.
CPC ........ *C07D 231/22* (2013.01); *A61K 31/4152* (2013.01); *A61K 31/4155* (2013.01); *A61K 31/485* (2013.01); *A61K 31/5377* (2013.01); *A61K 45/06* (2013.01); *C07D 401/12* (2013.01); *C07D 403/12* (2013.01); *C07D 471/04* (2013.01)

(58) Field of Classification Search
CPC ............ A61K 31/4152; A61K 31/4155; A61K 31/485; A61K 31/5377; C07D 231/22; C07D 401/12; C07D 403/12; C07D 471/04

See application file for complete search history.

(56) References Cited

U.S. PATENT DOCUMENTS

| | | |
|---|---|---|
| 2,908,677 A | 10/1959 | Straley |
| 3,514,439 A | 5/1970 | Wehrli et al. |
| 3,980,675 A | 9/1976 | Venturella et al. |
| 4,024,175 A | 5/1977 | Satzinger et al. |
| 4,207,392 A | 6/1980 | Shiao et al. |
| 4,234,479 A | 11/1980 | Mennicke et al. |
| 4,234,616 A | 11/1980 | Shu et al. |
| 4,337,263 A | 6/1982 | Techer et al. |
| 5,948,777 A | 9/1999 | Bender et al. |
| 6,057,371 A | 5/2000 | Glennon |
| 6,100,259 A | 8/2000 | Xiang et al. |
| 6,166,072 A | 12/2000 | Bell et al. |
| 6,451,857 B1 | 9/2002 | Hurtt et al. |
| 6,492,529 B1 | 12/2002 | Kapadia et al. |

(Continued)

FOREIGN PATENT DOCUMENTS

| | | |
|---|---|---|
| EP | 0248594 A2 | 12/1987 |
| EP | 0414289 A1 | 2/1991 |

(Continued)

OTHER PUBLICATIONS

Jianjing Cao, et al "Dual Probes for the Dopamine Transporter and sigma1 Receptors: Novel Piperazinyl Alkyl-bis (4-fluorophenyl)amine Analogues as Potential Cocaine-Abuse Therapeutic Agents", J. Med. Chem, No. 13, Mar. 20, 1946, pp. 2589-2598.

(Continued)

*Primary Examiner* — Sahar Javanmard
(74) *Attorney, Agent, or Firm* — Troutman Sanders LLP

(57) ABSTRACT

The invention relates to the use of a group of sigma receptor ligands of formula (I)

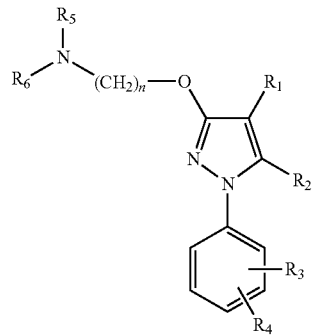

for the potentiation of the analgesic effect of opioids and opiates and at the same time for decreasing the dependency induced by them.

10 Claims, 7 Drawing Sheets

(56) References Cited

U.S. PATENT DOCUMENTS

| | | | |
|---|---|---|---|
| 6,509,367 | B1 | 1/2003 | Choon-Moon |
| 7,091,257 | B2 | 8/2006 | Greer, IV |
| 7,105,646 | B2 | 9/2006 | Chamberlain et al. |
| 7,696,199 | B2 | 4/2010 | Laggner et al. |
| 7,799,782 | B2 | 9/2010 | Munson et al. |
| 7,988,966 | B2 * | 8/2011 | Pavone ............. A61K 39/3955 424/130.1 |
| 8,193,223 | B2 | 6/2012 | Jagerovic et al. |
| 8,293,740 | B2 | 10/2012 | Laggner et al. |
| 8,314,096 | B2 | 11/2012 | Laggner et al. |
| 8,470,867 | B2 | 6/2013 | Laggner et al. |
| 8,492,425 | B2 | 7/2013 | Torrens et al. |
| 8,877,753 | B2 | 11/2014 | Buschmann |
| 2001/0036951 | A1 | 11/2001 | Farrar et al. |
| 2003/0144309 | A1 | 7/2003 | Choon-Moon |
| 2005/0020483 | A1 | 1/2005 | Oksenberg |
| 2006/0106068 | A1 | 5/2006 | Laggner |
| 2007/0208134 | A1 | 9/2007 | Hunter et al. |
| 2008/0058362 | A1 | 3/2008 | Singh et al. |
| 2008/0125416 | A1 | 5/2008 | Laggner et al. |
| 2008/0161604 | A1 | 7/2008 | Calvani et al. |
| 2009/0018151 | A1 | 1/2009 | Fink |
| 2009/0264442 | A1 | 10/2009 | Cuberes-Altisent et al. |
| 2009/0325975 | A1 | 12/2009 | Buschmann |
| 2010/0081659 | A1 | 4/2010 | Laggner |
| 2010/0190078 | A1 | 7/2010 | Rapaport et al. |
| 2010/0190780 | A1 | 7/2010 | Laggner et al. |
| 2010/0190781 | A1 | 7/2010 | Laggner et al. |
| 2010/0240711 | A1 | 9/2010 | Takada et al. |
| 2011/0112095 | A1 | 5/2011 | Buschmann et al. |
| 2011/0269727 | A1 | 11/2011 | Toledano |
| 2012/0141606 | A1 | 6/2012 | Baeyens-Cabrera et al. |
| 2012/0232093 | A1 | 9/2012 | Cuberes-Altisent et al. |
| 2012/0283262 | A1 | 11/2012 | Soler Ranzani et al. |
| 2012/0302568 | A1 | 11/2012 | Vela Hernandez et al. |
| 2012/0316336 | A1 | 12/2012 | Berenguer Maimo et al. |
| 2013/0109692 | A1 | 5/2013 | Vela Hernandez et al. |
| 2013/0143884 | A1 | 6/2013 | Cuberes-Aitisent et al. |
| 2013/0158033 | A1 | 6/2013 | Vela-Hernandez |
| 2013/0324535 | A1 | 12/2013 | Zamanillo-Castanedo et al. |
| 2015/0018354 | A1 | 1/2015 | Buschmann et al. |
| 2016/0220575 | A1 | 8/2016 | Baeyens-Cabrera et al. |

FOREIGN PATENT DOCUMENTS

| | | |
|---|---|---|
| EP | 0431943 A2 | 6/1991 |
| EP | 0445974 A2 | 9/1991 |
| EP | 0518805 A1 | 12/1992 |
| EP | 0529973 A1 | 3/1993 |
| EP | 0441333 | 5/1994 |
| EP | 0975648 A1 | 2/2000 |
| EP | 1130018 A1 | 9/2001 |
| EP | 1634872 A1 | 3/2006 |
| EP | 1634873 A1 | 3/2006 |
| EP | 1829866 A1 | 9/2007 |
| EP | 1829875 A1 | 9/2007 |
| EP | 1847542 A1 | 10/2007 |
| EP | 1787679 A1 | 11/2008 |
| EP | 2090311 A1 | 8/2009 |
| EP | 2112139 A1 | 10/2009 |
| EP | 2113501 A1 | 11/2009 |
| EP | 2116539 A1 | 11/2009 |
| EP | 2353598 A1 | 8/2010 |
| EP | 2254579 A1 | 12/2010 |
| EP | 2353591 A1 | 8/2011 |
| EP | 2361904 A1 | 8/2011 |
| EP | 2415471 A1 | 2/2012 |
| EP | 2292236 A1 | 3/2012 |
| EP | 2335688 A1 | 6/2012 |
| EP | 2460519 A1 | 6/2012 |
| EP | 2460804 A1 | 6/2012 |
| EP | 2524694 A1 | 11/2012 |
| EP | 2395003 A1 | 12/2012 |
| EP | 2426111 A1 | 3/2013 |
| EP | 2426112 A1 | 3/2013 |
| EP | 2792352 A1 | 10/2014 |
| EP | 2818166 A1 | 12/2014 |
| EP | 3043795 A1 | 7/2016 |
| EP | 3082790 A1 | 10/2016 |
| ES | 2251316 A1 | 10/2004 |
| FR | 2301250 A1 | 9/1976 |
| FR | 2472564 A1 | 7/1981 |
| GB | 1088973 A | 10/1967 |
| GB | 1496411 A | 12/1977 |
| GB | 2026482 A | 7/1987 |
| IL | 151533 B | 3/2008 |
| JP | 1992/364129 | 12/1992 |
| JP | 10036259 | 2/1998 |
| JP | 10055048 | 2/1998 |
| JP | 2004/196678 | 7/2004 |
| JP | 2008/510767 | 4/2008 |
| JP | 2008/179541 | 8/2008 |
| RU | 2218187 C2 | 10/2003 |
| RU | 2322977 C1 | 4/2008 |
| RU | 2382646 C1 | 2/2010 |
| SU | 11248 | 9/1929 |
| WO | WO-91/09594 A1 | 7/1991 |
| WO | WO-92/09560 A1 | 6/1992 |
| WO | WO-93/23383 A1 | 12/1992 |
| WO | 9616063 A1 | 5/1996 |
| WO | 9846618 A1 | 10/1998 |
| WO | WO-99/01444 A1 | 1/1999 |
| WO | WO-99/21824 A1 | 5/1999 |
| WO | WO-99/31057 A1 | 6/1999 |
| WO | WO-99/31074 A2 | 6/1999 |
| WO | WO-99/31075 A1 | 6/1999 |
| WO | 9959409 A1 | 11/1999 |
| WO | WO-99/61424 A1 | 12/1999 |
| WO | WO-00/31020 A1 | 2/2000 |
| WO | WO-00/20005 A1 | 4/2000 |
| WO | 00/27394 A1 | 5/2000 |
| WO | WO-00/40275 A2 | 7/2000 |
| WO | WO-00/73259 A1 | 12/2000 |
| WO | WO-00/73296 A2 | 12/2000 |
| WO | WO-00/73300 A1 | 12/2000 |
| WO | WO-02/085839 A1 | 10/2002 |
| WO | WO-02/092573 A2 | 11/2002 |
| WO | WO-02/102387 A1 | 12/2002 |
| WO | WO-2003/080183 A1 | 10/2003 |
| WO | WO-2004/016592 A1 | 2/2004 |
| WO | WO 2004/017961 A2 | 3/2004 |
| WO | WO-2004/046129 A2 | 6/2004 |
| WO | WO-2005/061462 A2 | 7/2005 |
| WO | WO-2006/010587 A1 | 2/2006 |
| WO | 2006021462 A1 | 3/2006 |
| WO | 2006027221 A1 | 3/2006 |
| WO | WO-2006/021463 A1 | 3/2006 |
| WO | WO-2006/118307 A1 | 11/2006 |
| WO | WO-2007/002559 A1 | 1/2007 |
| WO | WO-2007/025613 A2 | 3/2007 |
| WO | WO-2007/046550 A1 | 4/2007 |
| WO | WO-2007/079086 A1 | 7/2007 |
| WO | WO-2007/090661 A2 | 8/2007 |
| WO | 2007/098953 A1 | 9/2007 |
| WO | 2007/098963 A1 | 9/2007 |
| WO | WO-2007/098939 A1 | 9/2007 |
| WO | WO-2007/098964 A2 | 9/2007 |
| WO | WO-2007/108517 A1 | 9/2007 |
| WO | WO-2007/141018 A1 | 12/2007 |
| WO | WO-2008/015266 A1 | 2/2008 |
| WO | WO-2008/055932 A1 | 5/2008 |
| WO | WO-2008/108517 A2 | 9/2008 |
| WO | WO-2008/149062 A1 | 12/2008 |
| WO | WO-2009/038112 A1 | 3/2009 |
| WO | WO-2009/071657 A1 | 6/2009 |
| WO | WO-2009/103487 A1 | 8/2009 |
| WO | 2009130310 A1 | 10/2009 |
| WO | WO-2009/130314 A1 | 10/2009 |
| WO | WO-2009/130331 A1 | 10/2009 |
| WO | WO-2011/095579 A1 | 1/2011 |
| WO | WO-2011/018487 A1 | 2/2011 |
| WO | WO-2011/064296 A1 | 6/2011 |
| WO | WO-2011064315 A1 | 6/2011 |

(56) References Cited

FOREIGN PATENT DOCUMENTS

| WO | WO-2011/095585 A1 | 8/2011 |
|---|---|---|
| WO | WO-2011095584 A1 | 8/2011 |
| WO | WO-2011/144721 A1 | 11/2011 |
| WO | WO 2011/147910 A1 | 12/2011 |
| WO | WO-2012/016980 A1 | 2/2012 |
| WO | WO-2012/019984 A1 | 2/2012 |
| WO | WO 2012/072781 A1 | 6/2012 |
| WO | WO-2012/072782 A1 | 6/2012 |
| WO | WO-2012/156497 A1 | 11/2012 |
| WO | WO-2012/158413 A2 | 11/2012 |
| WO | WO 2014/170319 A1 | 10/2014 |
| WO | WO-2014/207024 A1 | 12/2014 |
| WO | WO 2015/036470 A1 | 3/2015 |
| WO | WO 2015036470 A1 | 3/2015 |
| WO | WO 2015/091505 A1 | 6/2015 |
| WO | WO 2015/091508 A1 | 6/2015 |

OTHER PUBLICATIONS

Nomura Mutsuko et al: "Studies on drug dependence (Rept. 322): Attenuation of morphine- and psychostimulants-induced place preference by sigma1 receptor agonist SA4503", Japanese Journal of Pharmacology, The Japanese Pharmacological Society, Kyoto, JP, vol. 79, No. suppl. 1, Jan. 1, 1999, p. 224P.

Sari Izenwasser et al: "Characterization of kappa-opioid receptor binding in human insular cortex", Life Sciences, Pergamon Press, Oxford, GB, vol. 65, No. 9, Jul. 23, 1999, pp. 857-862.

Osipova, N.A., "Tramadol (Tramal) in the Treatment of Acute and Chronic Pain Syndromes," Russky Meditsinsky Zhurnal (Russian Medicinal Journal), Feb. 25, 2003, No. 4, Sections: Pulmonology: Selected Lectures for Family Physicians (Retrieved from the Internet: URL<rmj.ru/number_36.htm).

D.G. Grahame-Smith et al. Oxford textbook on clinical pharmacology and drug therapy M., "Meditsina", 2000, pp. 658-661, Chapter "Narcotic analgesics".

Drug encyclopedia M., RLS 2001, pp. 572-573, articles "Morphine", "Morphine Sulfate".

Consilium MedSigma-receptors: new potentials of the treatment of depressions. Consilium Medicumicum 2012, vol. 14, No. 2 (found in the Internet: URL<new.Consiliummedicum.com/magazines/cm/medicum/article/21505, paragraphs 4-8).

Pirim, A et al.: "Addition of ketamine infusion to patient controlled analgesia with intravenous morphine after abdominal hysterectomy" Agri Jan. 2006; 18(1):52-8 Abstract.

Chien et al., Selective Antagonism of Opioid Analgesia by a Sigma System, J. Pharmacol. Exp. Ther.; 1994; 271; pp. 1583-1590.

Mei et al.; "Receptor Modulation of Opioid Analgesia in the Mouse", J. Pharmacol Exp. Ther.; 2002; 300(4); pp. 1070-1074.

Carlsson et al., "Interaction of pentobarbital and morphine in the tail-flick test performed on rates: synergism at the spinal and antagonism at the supraspinal level", NeuroSci. Lett.; 1986; 71; pp. 356-360.

Janicki et al., "Detection of Antagonist Activity for Narcotic Analgesics in Mouse Hot-Plate Test" Pharmacol. Biochem. Behavior, 1979; 10(4); pp. 623-626.

Chih-Cheng Chien et al., "Sigma antagonists potentiate opioid analgesia in rats", Neuroscience Letters, vol. 190, No. 2, 1995, pp. 137-139.

International Search Report for PCT/EP2009/054974, dated Jun. 17, 2009.

Whittington, C.M. et al. "Understanding and utilising mammalian venom via a platypus venom transcriptomen," J. Proteomics, 2009; vol. 72; pp. 155-164.

Wong et al., "Pentamorphone for management of postoperative pain," Anesth. Analg. May 1991, 72 (5): 656-60.

Written Opinion of the International Searching Authority dated Apr. 5, 2011 in connection with International Application No. PCT/EP2011/051644.

Written Opinion of the International Searching Authority dated Feb. 5, 2013 in connection with International Application No. PCT/EP2011/063286.

Written Opinion of the International Searching Authority dated Jun. 17, 2009 in connection with International Application No. PCT/EP2009/054974.

Yasuda, M. et al., Mast Cell Stabilization "Promotes Antinociceptive Effects in a Mouse Model of Postoperative Pain," J. Pain Res., 2013, vol. 6, pp. 161-166.

Zahn, P.K. et al., "Mechanisms for Pain Caused by Incisions", Regional Anesthesia and Pain Medicine, 2002, vol. 271 No. 5, pp. 514-516.

2007, XP002603149 Retrieved from the Internet:URL:http://web.archive.org/web/20080712205531/http://en.wikipedia.org/wiki/Opioidinduced-hyperalgesia. [retrieved on Oct. 1, 2010].

Acta Obstetrica Gynecologica Japonica, 2000, vol. 52 (6), pp. 117-120.

Advokat, c et al., "Selective antinociceptive effect of excitatory amino acid antagonists in intact and acute spinal rats," Pharmacology Biochemistry and Behavior 51(4):855-60 1995.

Angst, M.S. et al., "Opioid-induced Hyperalgesia: A Qualitative Systematic Review," Anesthesiology. vol. 104 pp. 570-587 (2006).

Anonymous "Opioid-Induced hyperalgesia," http://lweb.archive.org/web/20080712205531 /http://en.wikipedia.org/wiki/Opioid-inducedhyperalgesia (retrieved Feb. 16, 2017).

Arafa et. al., Journal of Medicinal Chemistry, 2005, American Chemical Society, vol. 48, pp. 5480-5488.

Brennan, T.J. et al., "Characterization of a rat model of incisional pain", Pain, 1996, vol. 64, pp. 493-501.

Bryant et al., Opioids and addiction: Emerging pharmaceutical strategies for reducing reward and opponent processes, Clinical Neuroscience Research, 2005, 5, pp. 103-115.

Buvanendran, A. et al. "Characterization of a New Animal Model for Evaluation of Persistent Postthoracotomy Pain", Anesth Analg, 2004, vol. 99, pp. 1453-60.

Celerier et al., "Progressive Enhancement of Delayed Hyperalgesia Induced by Repeated Heroin Administration: A Sensitization Process," The Journal of Neuroscience. vol. 21, No. 11 pp. 4074-4080 (2001).

Chen, S.R. et al. "Synergistic Effect between Intrathecal Non-NMDA Antagonist and Gabapentin on Allodynia Induced by Spinal Nerve Ligation in Rats", Anesthesiology, 2000, vol. 92, pp. 500-506.

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London. Series B, Biological Sciences, vol. 236, No. 1283, pp. 101-113.

Dosen-Micovic et. al., Bioorganic and Medicinal Chemistry, 2006, Elsevier, vol. 14, pp. 2887-2895.

Du, J. et al. "Kainate-induced Excitation and Sensitization of Nociceptors in Normal and Inflamed Rat Glabrous Skin", Neuroscience, 2006, vol. 137, pp. 999-1013.

Finnerup, N. B. et al. "The evidence for pharmacological treatment of neuropathic pain", Pain, 2010, vol. 150, pp. 573-581.

Glass et al., "Evaluation of pentamorphone in humans: a new potent opiate," Anesth. Analg. Mar., 1989, 68(3) 302-7.

Guignard et al., "Acute Opioid Tolerance: Intraoperative RemifentanilIncreases Postoperative Pain and Morphine Requirement," Anesthesiology, vol. 93 pp. 409-417 (2000).

Hellewell, S.B. et al., "A sigma-likebinding site in rat pheochromocytoma (PC12) cells: decreased affinity for (+)-benzomorphans and lower molecular weight suggest a different sigma receptor form from that of guinea pig brain," Brain Research, vol. 527.

Hiranita et al., "Reinforcing effects of sigma-receptor agonists in rats trained to self-administer cocaine," J Pharmacol Exp Ther. Feb. 2010; 332(2):515-524 (2010).

International Preliminary Report on Patentability dated Aug. 7, 2012 in connection with International Application No. PCT/EP2011/051644.

(56) References Cited

OTHER PUBLICATIONS

International Preliminary Report on Patentability dated Feb. 3, 2013 in connection with International Application No. PCT/EP2011/063286.
International Preliminary Report on Patentability dated Oct. 26, 2010 in connection with International Application No. PCT/EP2009/054974.
International Search Report issued by International Searching Authority dated Jan. 31, 2012 in connection with International Application No. PCT/EP2011/063286.
International Search Report issued by the International Searching Authority dated Apr. 5, 2011 in connection with International Application No. PCT/EP2011/051644.
Kawamata, M. et al. "Experimental incision-induced pain in human skin: effects of systemic lidocaine on flare formation and hyperalgesia", Pain, 2002, vol. 100, pp. 77-89.
Kehlet, H et al., "Anaesthesia, surgery, and challenges in postoperative recovery", Lancet 2003, vol. 362, pp. 1921-28.
Kehlet, H. et al. "Persistent Surgical Pain: Risk Factors and Prevention", Lancet, 2006, vol. 367; pp. 1618-25.
Kehlet, H. et al. "PROSPECT: evidence-based, procedure-specific postoperative pain management", Best Practice Res Clin Anaesthesiol., 2007, vol. 21, pp. 149-159.
Kenakin, A Pharmacology Primer, The Evolving Pharmacology of GPCR's, 2006, pp. 27-60.
Laggner et al. "Discovery of High-Affinity Ligands of Sigma Receptor, ERG2, and Emopamil Binding Protein by Pharmacophore Modeling and Virtual Screening", J. Med. Chem., 2005, vol. 48, pp. 4754-4764.
Lee, M. et al., "A Comprehensive Review of Opioid-Induced Hyperalgesia," Pain Physician. vol. 14 pp. 145-161 (2011).
Leitner et al., "Regional variation in the ratio of o1 to a2 binding in rat brain," European Journal of Pharmacology, vol. 259 pp. 65-69 (1994).
Levine, J.D. et al. "Desiperamide Enhances Opiate Postoperative Analgesia", Pain, 1986, vol. 27, pp. 45-49.
Lytle et al. "Effects of long-term corn consumption on brain serotonin and the response to electric shock," Science vol. 190 pp. 692-694 (1975).
Mao, J., "Opioid-induced abnormal pain sensitivity: implications in clinical opioid therapy," Pain. vol. 100 pp. 213-217 (2002).
Max, M.B. et al. "Endogenous Monoamine Analgesic Systems: Amitriptyline in Painful Diabetic Neuropathy", Anesth. Prog., 1987, vol. 34, pp. 113-127.
Merskey, H. et al., IASP Classification of Chronic Pain, 2002, 2nd edition, pp. 210-213.
Office Action and Search Report corresponding to Taiwanese Patent Application No. 100127236 (Translation) [undated].
Prasad et al., "Exon-Intron Structure, Analysis of Promoter Region, and Chromosomal Localization of the Human Type 1 σ Receptor Gene," Journal of Neurochemistry. vol. 70 pp. 443-451 (1998).
Quirion et al., "A proposal for the classification of sigma binding sites," Trends pharmacal. Sci. vol. 13 pp. 85-86 (1992).
Ronsisvalle et al., "Opioid and sigma receptor studies. New development in the design of selective sigma ligands," Pure Appl. Chem. vol. 73, No. 9 pp. 1499-1509 (2001).
Saha et al., "Spinal Mitogen-Activated Protein Kinase Phosphatase (MKP-3) Is Necessary for the Normal Resolution of Mechanical Allodynia in a Mouse Model of Acute Postoperative Pain", J.Neurosci., 2013, vol. 43, pp. 17182-17187.
Sandford, M., et al.; Pain Physician 2009; 12:679-684.
Silveverman, M., "Opioid Induced Hyperalgesia: Clinical Implications for the Pain Practitioner," Pain Physician. vol. 12 pp. 679-684 (2009).
Smith M.T., "Opioid-induced hyperalgesia, opioid rotation and opioid combinations," Acute Pain. vol. 10 pp. 199-200 (2008) [Abstract].

Trescot et al., "Opioids in the Management of Chronic Non-Cancer Pain: An Update of American Society of the Interventional Pain Physicians' (ASIPP) Guidelines," Pain Physician. Opioids Special Issue: 11 pp. S5-S62 (2008).
Wang, "Opioid-induced hyperalgesia", Chinese Journal of Pain Medicine, 14(3), pp. 129-130 (2008).
"Chemotherapy at home, pain and its treatment", Soins, Office De Publicite Generale, Paris, FR, (19890901), No. 528, ISSN 0038-0814, pp. 17-20, XP009107313 [A] 1-16. * p. 19 *.
Aapro, M. et al., "Anticipatory Nausea and Vomiting", Support Care Cancer, 2005, vol. 13, pp. 117-121.
Abadias, M. et al. "Saftey, Tolerability and Pharmacokinetics of Single and Multiple Doses of a Novel Sigma-1 Receptor Antagonist in Three Randomized Phase I studies," British Journal of Clinical Pharmacology, 2012, 75:1, 103-117.
Abbott, C, A., et al., "The North-West Diabetes Foot Care Study: incidence of, and risk factors for, new diabetic foot ulceration in a community-based patient cohort", Diabetic Medicine, vol. 19, 2002, pp. 377-384.
Abraham, D.J., et al., "Burger's Medicinal Chem istry: Drug Discovery and Development" 7th edition, 8 volume set, 2010.
Abrams, P., et al., "The standardisation of terminology of lower urinary tract function: report from the standardisation sub-committee of the International Continence Society", Neurology and Urodynamics, 21, 2002, pp. 167-178.
Alberts, D.S., et al., "Cisplatin-associated neurotoxicity: can it be prevented?" Anti-cancer Drugs, 1995, vol. 6, pp. 369-383.
Almerico, AM., "1-Methyi-3H-pyrazolo[1, 2-a]benzo[1, 2, 3, 4] tetrazin-3-ones: Design, synthesis and biological activity of new antitumor agents", Journal of Medicinal Chemistry, vol. 48, 2005, pp. 2859-2866.
Anderson, B. D. et al., "Preparation of Water-Soluble Compounds Through Salt Formation" The Practice of Medicinal Chemistry, Chapter 34, pp. 739-754 (1996).
Anton, E., "Delayed toxicity of cyclophosphamide on the bladder of DBA/2 and C57BL/6 female mouse," Int. J. Exp. Path., 83, 2002, pp. 47-53.
Arthritis [online], [retrieved on Nov. 20, 2007]. Retrieved from the Internet, URL; http://www.nlm.nlh.gov/medlineplus/ency/article/001243.htm>.
Argyrioul, A.A., et al., "Bortezomib-induced peripheral neuropathy in multiple myeloma: a comprehensive review of the literature", Blood, 2008, vol. 112, No. 5, pp. 1593-1599.
Asano, T., et al. Antinociception by epidural and systemic alpha(2)adrenoceptor agonists and their binding affinity in rat spinal cord and brain, Anesth Anal g.2000; 90 (2): 400-407.
Baraldi, et al., "Ethyl 2, 4-Dioxoalkanoates as Starting Materials for a Convenient Route to 3(2H)Furanones and 3(2H) Furanimines", Tetrahedron, vol. 43, No. 1, pp. 235-242, 1987.
Baraldi, et al., "Ethyl 5-Substituted-3-Isoxazolecarboxylates as Starting Materials for a Convenient Route to 3(2H) Furanones and 3(2H)Iminofuranes", Tetrahedron Lett., 25(38), pp. 4313-4316; 1984.
Barnes, J.M. et al., "Reserpine, *Para*-Chlorophenylalanine and Fenfluramine Antagonise Cisplatin-Induced Emesis in the Ferret", Neuropharmacology, 1988, vol. 27, No. 8, pp. 783-790.
Batson, et al., "a-Hydroxy Cyclopentenones from a-Diketones", Organic Letters, vol. 7, No. 13, pp. 2771-2774, 2005.
Beaudegnies, R., et al. "Design and synthesis of novel spirocyclopropyl cyclohexane-1,3-diones and -1,3,5-triones for their incorporation into potent HPPD inhibitors", Tetrahedron Letters, 2010, vol. 51, pp. 2741-2744.
Bennett, G. J. "Pathophysiology and Animal Models of Cancer-Related Painful Peripheral Neuropathy", The Oncologist, 2010, 15 (suppl2), pp. 9-12.
Berge, S.M. et al., "Pharmaceutical Salts," Journal of Pharmaceutical Sciences, 1977, vol. 66, No. 1, pp. 1-19.
Bon, K., et al., "Characterization of cyclophosphamide cystitis, a model of visceral and referred pain, in the mouse: species and strain differences.", J UROL., (2003), vol. 170, No. 3, pp. 1008-1012.
Botting, R.M.; Clinical Infectious Diseases, 2000, 31, S202-10.
Boulton, A.J.M., et al., "Diabetic Neuropathies" Diabetes Care, vol. 28, No. 4, Apr. 2005, pp. 956-962.

(56) References Cited

OTHER PUBLICATIONS

Bowen W. D., Pharmaceutica *Acta Helvetiae*; 2000; 74:211-218.
Brammer et al. in European Journal of Pharmacology, 553, 141-145 (2006).
Brennan, T.J., et al., "Characterization of a rat model of incisional pain", Pain, 1996, vol. 64, pp. 493-501.
Brussee, et al., Diabetes, 2008, 57: 1664-1673, "Distal Degenerative Sensory Neuropathy in a Long-Term Type 2 Diabetes Rat Model".
Bryans, J.S., et al., "3-substituted GABA analogs with central nervous system activity: a review," Med Res Rev, 19, 1999, pp. 149-177.
Bryans, J.S., et al., "Identification of novel ligands for the gabapentin binding site on the alpha-2-delta subunit of a calcium channel and their evaluation as anticonvulsant agents", J. Med. Chern. 41, 1998, pp. 1838-1845.
Buerkle, H., Yaksh, T. L. Pharmacological evidence for different alpha 2-adrenergic receptor sites mediating analgesia and sedation in the rat, *Br J Anaesth*.1998; 81 (2): 208-215.
Bura, S.A. et al., "Evaluation of the Effect of the Selective Sigma-1 Receptor Antagonist Sira in Neuropathic Pain Using an Operant Model", Eur J. Pain Supplements 2010, vol. 4, p. 49 (Abstract Only).
Cancer [online], [retrieved on Jul. 6, 2007]. Retrieved from the Internet, URL; http://www.nim.nih.gov/medlineplus/cancer.html>.
Lala et al., "Role of Nitric Oxide in Tumor Progression: Lessons from Experimental Tumors," Cancer and Metastasis Reviews, 17(1), 91-106, 1998.
Carrie, et al., Int Orthopaedics vol. 30, pase 445-451. publication year: 2006.
Carter, N., et al., "Duloxetine: a review of its use in the treatment of generalized anxiety disorder.", CNS Drugs 2009, (2009), vol. 23, No. 6, ISSN 1172-7047, pp. 523-541, ISSN: 1172-7047.
Case 07 "Joint Pain and Muscle Pain", Nurse Beans — Smart Nurse, Nov. 2007, vol. 9, No. II, pp. 1238-1239.
Cepeda, MS, "Comparison of Morphine, ketorolac, and their combination for postoperative pain: results form a large, randomized, double-blind trial", anesthesiology, 2005, vol. I03, No. 6, pp. I225-I232.
Cersosimo, R.J., "Oxaliplatin-Associated Neuropathy: A Review", The Annals of Pharmacotherapy, 2005 vol. 39 pp. 128-135.
Chaplan S. R., et al., "Quantitative assessment of tactile allodynia in the rat paw", J. Neurosci. Methods, (1994), vol. 53, pp. 55-63.
Chaudhry, V., et al., "Bortezomib and thalidomide-induced subacute demyelinating polyneuropathy," Clinical Neurophysiology, 2009, vol. 120, p. e111.
Chaudhry, V., et al., "Peripheral Neuropathy from Taxol and Cisplatin Combination Chemotherapy: Clinical and Electrophysiological Studies", Annals of Neurology, 1994, vol. 35, No. 3, pp. 304-311.
Cheng, et al., Modern Bone Science, Modern Orthopaedics, "14.2.2 Drug Analgesia," p. 164, 2010, including English translation.
Chen, D., et al., "Development and application of rodent models for type 2 Diabetes", Diabetes, Obesity and Metabolism, vol. 7, 2005, pp. 307-317.
Cherny, N., "Opioids and The Management of Cancer Pain", Eur. J. Cancer Supplement 2005, vol. 3, pp. 61-75.
Chichenkov, O.N. et al., "Effect of haloperidol on the analgesic activity of intracisternally and intrathecally injected opiate agonists," Farmakologiya I Toksikologiya, (1985), vol. 48. 48, No. 4, pp. 58-61.
Cited ref STN search abstract JP10055048.
Clark, J.B., et al., "The Diabetic Zucker Fatty Rat (41611)", Proceedings of the society for experimental Biology and Medicine, 1983, vol. 173, pp. 68-75.
Cobos, E. J., et al., Pharmacology and therapeutic potential of Sigma(1) receptor ligands. *Curr. Neuropharmacol*.2008; 6, 344-366.
Final Office Action as dated Nov. 29, 2007 in related priority U.S. Appl. No. 10/978,250.

Final Office Action as dated Oct. 20, 2008 in related priority U.S. Appl. No. 10/978,250.
Non-Final Office Action as dated Apr. 16, 2008 in related priority U.S. Appl. No. 10/978,250.
Non-Final Office Action as dated Jun. 14, 2007 in related priority U.S. Appl. No. 10/978,250.
Requirement for Restriction/Election as dated Apr. 5, 2007 in related priority U.S. Appl. No. 10/978,250.
Coxon, et al., "Acid-catalysed Rearrangements of trans- and cis-1-Acetoxy-3,4-epoxypentane and 1-Acetoxy-4,5- epoxyhexane", J. Chem. Soc. Chem. Commun., 8, pp. 261-262, 1973.
Crawford, K.W.et al., "Sigma-2 Receptor Agonists Activate a Novel Apoptotic Pathway and Potentiate Antineoplastic Drugs in Breast Tumor cell Lines1," Cancer Research, 2002, vol. 62, pp. 313-322.
D'Amour, F. E. And Smith, D. L. A method for determining the loss of pain sensation, *J. Pharmacal. Exp. Ther*.1941; 72:74-79.
Dani, et al. (2007) The local antinociceptive effects of paracetamol in neuropathic pain are mediated by cannabinoid receptors. European Journal of Pharmacology 573(1-3): 214-215.
Daousi, C., et al., "Chronic painful peripheral neuropathy in an urban community: a controlled comparison of people with and without diabetes", Diabetic Medicine, vol. 21, 2004, pp. 976-982.
Dapeng Li "The Role of Glial Cells in . . . Pain", Thesis of Huazhong, University of Science and Technology, 2006, p. 24; Publication Date: Feb. 19, 2008.
Database WPI Week 200451 Thomson Scientific, London, GB; AN 2004-529624-& JP 2004 196678 A (Dainippon Pharm Co Ltd) Jul. 15, 2004 (Jul. 15, 2004).
Dauben, W., et al., "Organic Reactions at High Pressure Preparation of Wittig Phosphonium Salts at Ambient Temperature", J. Org. Chern., 1984, vol. 49, pp. 4293-4295.
Davies, A., et al., "Functional biology of the alpha-2-delta subunits of voltage-gated calcium channels,"trends in Pharmacological Sciences, vol. 28, No. 5, 2007, pp. 220-228.
DeHaven-Hudkins, et al., "Characterization of the binding of [ H](+)-pentazocine to σ recognition sites in guinea pig brain," European Journal of Pharmacology- Molecular Pharmacology Section, 1992, vol. 227, pp. 371-378.
Dewar, "Diethyl-[3-(5-methyl-1-phenyl-1H-pyrazol-3-yl)-propyl]amine", Database Beilstein, Beilstein Institute for Organic Chemistry, Frankfurt-Main, DE, Database accession No. 213356, XP002605612 [X] 1-3,5,6,9. * the whole document *.
Dewar, M. J. S., "Attempts to find new Antimalarials. Part XXI", Journal of the Chemical Society, (1944), pp. 615-619.
Dias, V. C., et al., Clinical experience with transdermal clonidine in African-American and Hispanic-American patients with hypertension: evaluation from a 12-week prospective, open-label clinical trial in community-based clinics, Am J Ther. 1999; 6 (1): 19-24.
Diaz, J.L. et al., "Selective Sigma-1 Receptor Antagonists: Emerging Target for the Treatment of Neuropathic Pain", Cent. Nerv. Syst. Agents in Med. Chem. 2009, vol. 9 pp. 172-183.
Díaz, J.L., et al., "Synthesis and Biological Evaluation of the 1-Arylpyrazole Class of sigma 1 Receptor Antagonists: Identification of 4-{2-[5-Methyl-1-(naphthalen-2-yl)-1 H -pyrazol-3-yloxy]ethyl}morpholine (S1RA, E-52862)", Journal of Medicinal Chemistry, (20121011), vol. 55, No. 19, doi:10.1021/jm3007323, ISSN 0022-2623, pp. 8211-8224, XP055094581 [Y] 1-14,16 * abstract ** p. 8219, col. left, paragraphs 3-4 *.
Dixon, W. J., "Efficient analysis of experimental observations", Ann. Rev. Pharmacal. Toxicol., 20,1980, pp. 441-462.
Dmitrieva, N., et al., "The role of nerve growth factor in a model of visceral inflammation", Neuroscience, vol. 78, No. 2, 1997, pp. 449-459.
Dougherty, P.M., et al. "Taxol-induced sensory disturbance is characterized by preferential impairment of myelinated fiber function in cancer patients", Pain, 2004, vol. 109, pp. 132-142.
Dugowson, et al.; Phys. Med. Rehabil. Clin. N. Arn. 2006, 17, 347-354.
Dukic-Ott, A. "Production of pellets via extrusion spheronisation without the incorporation of microcrystalline cellulose: A critical review," European Journal of Pharmaceutics and Biopharmaceutics, 2009, vol. 71, pp. 38-46.

(56) References Cited

OTHER PUBLICATIONS

Dunlap, B., et al., "Chemotherapy-Induced Peripheral Neuropathy Measurement", The Journal of Supportive Oncology, 2006, vol. 4, 8, pp.
Dworkin R.H., "An Overview of Neuropathic Pain: Syndromes, Symptoms, Signs, and Several Mechanisms," The Clinical Journal of Pain 2002, vol. 18, pp. 343-349.
Dworkin, R.H. et a., "Recommendations for Ihe Pharmacological Management of Neuropathic Pain: Literature Update", Mayo Clin. Proc., 2010, 85(3)(Suppl), S3-S14.
Effenberger, F., et al., Chem. Ber., 102(10), 3260-3267, 1969.
Eghbaldar, et al., "Substances aromatisantes separation chirale par chromatographie gazeuse" Parfums, Cosmetiques, Aromes, 104, pp. 71-78, 1992.
Eisenach, J. C., et al., Intrathecal, but not intravenous, clonidine reduces experimental thermal or capsaicin-induced pain and hyperalgesia in normal volunteers; Anesth Analg; 1998; 87: 591-596.
Entrena, J.M., et al., "Sigma-I receptors are essential for capsaicin-induced mechanical hypersensitivity: Studies with selective sigma-1 ligands and sigma-1 knockout mice", PAIN, (2009), vol. 143, pp. 252-61.
Epilepsy [online], [retrieved on Nov. 20, 2007]. Retrieved from the Internet, URL; http://www.nim.nih.gov/medlineplus/ ency/ article/ 000694.htm>.
Epstein, et al., "Oral Doxepin Rinse: The Analgesic Effect and Duration of Pain Reduction in Patients with Oral Mucositis Due to Cancer Therapy" (2006) Pain Medicine, vol. 103, No. 2, pp. 465-470.
Epstein, et al., "Oral topical doxepin rinse: analgesic effect in patients with oral mucosal pain due to cancer or cancer therapy" (2001) Oral Oncology, 37:632-637.
European Search Report dated Feb. 1, 2005 in connection with priorirty European Application No. EP 04077421.8.
European Search Report dated Apr. 19, 2010 in connection with European Application No. EP10382024.7.
European Search Report dated Dec. 20, 2013 in connection with European Application No. EP13382246.0.
European Search Report dated Feb. 5, 2010 in connection with European Application No. EP09382144.
European Search Report dated Jan. 31, 2011 in connection with European Patent Application No. 10382326.6.
European Search Report dated Jul. 1, 2010 in connection with European Patent Application No. EP10382025.
European Search Report dated Jun. 16, 2010 in connection with European Application No. EP 10382023.
European Search Report dated Mar. 11, 2011 in connection with European Application No. EP10382330.8.
European Search Report dated Apr. 14, 2010 in connection with European Application No. EP09382261.
European Search Report dated May 3, 2013 in connection with European Patent Application No. EP13382140.
European Search Report dated Oct. 1, 2010 in connection with European Application No. EP10382215.1.
European Search Report dated Oct. 18, 2011 in connection with European Application No. EP11382157.3.
European Search Report dated Oct. 2, 2008 in connection with European Application No. EP 08380122.
European Search Report dated Oct. 29, 2010 in connection with European Application No. EP10382136.
European Search Report dated Sep. 12, 2008 in connection with European Application No. EP08384006.
Extended European Search report dated Oct. 22, 2010 by European Patent Office in connection with European Application No. EP 10 38 2148.
Falk et al. "Pain and Nociception: Mechanisms of Cancer-Induced Bone Pain", Journal Clinical Oncology, 2014, vol. 32, pp. 1647-1654.
Field, M.J., et al., "Identification of the alpha-2-delta-1 subunit of voltage-dependent calcium channels as a molecular target for pain mediating the analgesic actions of pregabalin", PNAS, vol. 103, No. 46, Nov. 14, 2006, pp. 17537-17542.
Forsyth, P.A., et al., "Prospective study of paclitaxel-induced peripheral neuropathy with quantitative sensory testing", Journal of Neuro-Oncology, 1997, vol. 35, pp. 47-53.
Friedman, J.E., et al., Altered expression of muscle glucose transporter GLUT-4 in diabetic fatty Zucker rats (ZDF/DRTFA), American Physiological Society, 1991, E782-E788.
Gabriel, A.F., Preoperative housing in an enriched environment significantly reduces the duration of post-operative pain in a rat model of knee inflammation, Neurosci. Lett. 2010, vol. 469, No. 2, pp. 219-232.
Gauchan, P., et al., "Mechanical Allodynia Induced by Pacli taxel, oxaliplatin and Vincristine: Different Effectiveness of Gabapentin and Different Expression of Voltage-Dependent Calcium Channel a26-1 subunit", Biol. Phann. Bull., 2009, vol. 32, No. 4 ƒ pp. 732-734.
Gentili, M., et al., "Intra-articular morphine and clonidine produce comparable analgesia but the combination is not more effective, Br J Anaesth.1997; 79 (5): 660-661.
Goblirsch, M.J., et al., "Biology of Bone Cancer Pain," Clin. Cancer Res. 2006' vol. 12 (20 Suppl.), pp. 6231s-6235s.
Goodman, et al., "The Pharmacological Basis of Therapeutics", 8th Ed.; 13-18. , 1992.
Gordois, a., et al., "The Health Care Costs of Diabetic Peripheral Neuropathy in the U.S.", Diabetes Care, vol. 26, No. 6, Jun. 2003, pp. 1790-1795.
Gordon, A.N., et al., "Phase 1 Dose Escalation of Paclitaxel in Patients with Advanced Ovarian Cancer Receiving Cisplatin: Rapid Development of Neurotoxicity is Dose-Limiting", Journal of Clinical Oncology, 1997, vol. 15, No. 5, pp. 1965-1973.
Gralla et al. in Annals of Internal Medicine 95(4), 414-420 (1981).
Grover, S., et al., "Role of inflammation in bladder function and interstitial cystitis", Therapeutic Advances in Urology, 3(1 ), 2011, pp. 19-33.
Grunberg, S, M., et al., "Incidence of Chemotherapy-Induced Nausea and Emesis after Modern Antiemetics," Cancer, 2004, vol. 100, pp. 2261-2268.
Guitart, X., et al., "Sigma receptors biology and therapeutic potential", Psychophamacology, 2004, vol. 17 4, pp. 301-319.
Haleblian, "Characterization of Habits and Crystalline Modification of Solids and Their Pharmaceutical Applications," Journal of Pharmaceutical Sciences, vol. 64, No. 8 pp. 1269-1288 (1975).
Hall, J. E., Uhrich, T. D., Ebert, T. J. Sedative, analgesic and cognitive effects of clonidine infusions in humans, Br J Anaesth. 2001; 86 (1 ): 5-11.
Hammack, et al., "Phase III evaluation of nortriptyline for alleviation of symptoms of cis-platinum-induced peripheral neuropathy" (2002) Pain, 98:195-203.
Hancock, et al., "Characteristics and Significance of the Amorphous State in Phamnaceutical Systems," Journal of Phamnaceutical Sciences, vol. 86, No. 1 pp. 1-12 (1997).
Hanno, Philip, "International Consultation on IC—Rome, Sep. 2004/Forging an interenational consensus: progress in painful bladder syndrome/interstitial cystitis", Int Urogynocol J, 16, 2005, pp. S2-S34.
Harden, N., et al., "Unmet Needs in the Management of Neuropathic Pain", Journal of Pain and Symptom Management, 2003, 25, 5S, S12-S17.
Hartwig, J., "Synthesis, Structure, and Reactivity of a Palladium Hydrazonato Complex: A New Type of Reductive Elimination Reaction to FormC-N Bonds and Catalytic Arylation of Benzophenone Hydrazone", Angew. Chem. Int. Ed., 1998, vol. 37, No. 15, pp. 2090-2093.
Hayashi, T., et al., "Sigma-1 receptor ligands: potential in the treatment of neuropsychiatric disorders," CNS Drugs. 2004;18(5) :269-84.
Hecht, J. R. et al., "Prolonged Nausea and Vomiting after High Dose Chemotherapy and Autologous Peripheral Stem Cell Transplantation in the Treatment of High Risk Breast Carcinorrta," Cancer, 19971 vol. 7 9' pp. 1698-1702.
Herndon, et al.; Pharmacotherapy, 2008, 28(6), 788-805.

(56) References Cited

OTHER PUBLICATIONS

Herrstedt, J., et al., \'Acute emesis moderately emetogenic chemoc. herapy, Support Care Cancer, 2005, vol. 13, pp. 97-103.
Hesketh, M.' et al., "Proposal for classifying the Acute Emetogenicity of Cancer Chemotherapy", Journal of Clinical Oncology, 1997, vol. 15, pp. 103-109.
Hidaka, T., et al., W5-7 "A Basic Study of the Effect Peony Licorice Water on Paclitaxel-Induced Pain in Mice", Japan Academic Journal of Cancer Treatment, Sep. 2009, vol. 44, No. 2, p. 323 [inc. machine English language translation).
Hileman, G.A., et al., "Response surface optimization of high dose pellets by extrusion and spheronization," International Journal of Pharmaceutics, 1993, vol. 100, pp. 71-79.
Hinz et al., FASEB Journal, 2007, 7, 2343-2351.
Narujo, Hiroyuki, et al., Cancer Pain Treatment — Clinical Oral Morphine Extended-Release Tablets (once/day), $5^{th}$, Pharma Medical, 2007, including English language translation.
Homer, et al., "Azo-aryle and Phenazine aus primaren Arylaminanionen durch Autoxydation", Chern. Ber, 96, pp. 786-793, 1963.
Hsu, et al., Toxic. Appl. Pharmac., vol. 73, No. 3, pp. 411-415, 1984.
Hudzik T. J., "Sigma Ligand-Induced Emesis in the Pigeon," Pharmacology Biochemistry & Behavior, 1991, 41(1), pp. 215-217.
Hudzik, T., et al., "o Receptor-mediated emetic response in pigeons: agonists, antagonists and modifiers", European Journal of Pharmacology, 1993, vol. 236, pp. 279-287.
IASP Classification of Chronic Pain, 2002, 2nd edition, pp. 201-213.
International Preliminary Report of Patentability with Written Opinion of the International Searching Authority dated Nov. 27, 2012 in connection with International Application No. PCT/EP2011/058633.
International Preliminary Report of Patentability with Written Opinion of the International Searching Authority dated Feb. 14, 2012 in connection with International Application No. PCT/EP2010/061720.
International Preliminary Report of Patentability with Written Opinion of the International Searching Authority dated May 30, 2012 in connection with International Application No. PCT/EP2010/068213.
International Preliminary Report of Patentability with Written Opinion of the International Searching Authority dated Feb. 12, 2013 in connection with International Patent Application No. PCT/EP2011/063583.
International Preliminary Report of Patentability with Written Opinion of the International Searching Authority dated Aug. 7, 2012 in connection with International Application No. PCT/EP11/51643.
International Preliminary Report of Patentability with Written Opinion of the International Searching Authority dated Aug. 24, 2010 in connection with International Application No. PCT/EP2009/001109.
International Preliminary Report of Patentability with Written Opinion of the International Searching Authority dated Dec. 29, 2015 in connection with International Application No. PCT/EP2014/063360.
International Preliminary Report of Patentability with Written Opinion of the International Searching Authority dated Feb. 28, 2007 in connection with International Application No. PCT/EP2005/009375.
International Preliminary Report of Patentability with Written Opinion of the International Searching Authority dated Jun. 21, 2016 in connection with International Application No. PCT/EP2014/077996.
International Preliminary Report of Patentability with Written Opinion of the International Searching Authority dated Jun. 21, 2016 in connection with International Application No. PCT/EP2014/077992.
International Preliminary Report of Patentability with Written Opinion of the International Searching Authority dated Jun. 4, 2013 in connection with International Application No. PCT/EP2011/071584.
International Preliminary Report of Patentability with Written Opinion of the International Searching Authority dated Jun. 26, 2012 in connection with International Application No. PCT/EP2012/059232.
International Preliminary Report of Patentability with Written Opinion of the International Searching Authority dated Mar. 15, 2016 in connection with International Applications No. PCT/EP2014/069370.
International Preliminary Report of Patentability with Written Opinion of the International Searching Authority dated May 30, 2012 in connection with International Application No. PCT/EP2010/068256.
International Preliminary Report of Patentability with Written Opinion of the International Searching Authority dated Nov. 27, 2012 in connection with International Applications No. PCT/EP2011/058224.
International Preliminary Report of Patentability with Written Opinion of the International Searching Authority dated Oct. 20, 2015 in connection with International Application No. PCT/EP2014/057608.
International Search Report dated Jul. 24, 2009 in connection with International Application No. PCT/EP2009/054981.
International Search Report dated Nov. 25, 2010 in connection with International Application No. PCT/EP2010/061720.
International Search Report dated May 4, 2011 in connection with International Application No. PCT/EP2011/051630.
International Search Report dated Aug. 31, 2011 in connection with International Application No. PCT/EP2011/063583.
International Search Report dated May 4, 2011 in connection with International Application No. PCT/EP2010/068256.
International Search Report dated Sep. 21, 2011 in connection with International Application No. PCT/EP2011/058633.
International Search Report dated Feb. 25, 2015 in connection with International Application No. PCT/EP2014/077996.
International Search Report dated Jan. 12, 2005 in connection with International Application No. PCT/EP2005/009375.
International Search Report dated Jan. 16, 2012 in connection with International Application No. PCT/EP2001/071583.
International Search report dated Jul. 7, 2009 in connection with International Application No. PCT/EP2009/001109.
International Search Report dated Jun. 26, 2012 in connection with International Application No. No. PCT/EP12/59232.
International Search Report dated Mar. 13, 2012 in connection with International Application No. PCT/EP2011/071584.
International Search Report dated Mar. 23, 2011 in connection with International Application No. PCT/EP2010/068213.
International Search Report dated Mar. 6, 2014 in connection with International Application No. PCT/EP2014/057608.
International Search report dated May 23, 2011 in connection with International Application No. PCT/EP11/51643.
International Search report dated Oct. 31, 2014 in connection with International Application No. PCT/EP2014/069370.
International Search report dated Sep. 17, 2014 in connection with International Application No. PCT/EP2014/063360.
International Search Report dated Sep. 3, 2015 in connection with International Application No. PCT/EP2014/077992.
International Search Report dated Mar. 8, 2011 in connection with International Applications No. PCT/EP2011/058224.
International Preliminary Report of Patentability with Written Opinion of the International Searching Authority dated Oct. 26, 2010 in connection with International Application No. PCT/EP2009/054981.
Isakov "The problem of pain in oncology", Russian Medicinal Journal, 2000, vol. 17, pp. 723-727.
Isomers [on-line], [retrieved on Mar. 11, 2007]. Retrieved from the Internet, URL; http://chemed.chem. purdue.edu/genchem/topicreview/bp/1organic/isomers .html>.
Jordan, K., et al. "Chemotherapy-induced nausea and vomiting: current and new standards in the antiemetic prophylaxis and treatment," Eur J Cancer. Jan. 2005;41 (2) :199-205.

(56) References Cited

OTHER PUBLICATIONS

Jover, I., et al., "Evaluation, by a Statistically Designed Experiment, of an Experimental Grade of Microcrystalline Cellulose, Avicel 955, as a Technology to Aid to Production of Pellets with High Drug Loading," Journal of Pharmaceutical Sciences, 1996, vol. 85, No. 71 pp. 700-705.
Kaiser, et al., *Neurotransmissions*; 1991; 7(1); 1-5.
Kautio, et al., "Amitriptyline in the Prevention of Chemotherapy-induced Neuropathic Symptoms" (2009) Anticancer Research, 29:2601-2606.
Kautio, et al., "Amitriptyline in the Treatment of Chemotherapy-Induced Neuropathic Symptoms" (2008) Journal of Pain and Symptom Management, 35(1) :31-39.
Kadiroglu, A.K., et al., "The effect of venlafaxine HCl on painful peripheral diabetic neuropathy in patients with type 2 diabetes mellitus.", Journal of Diabetes and Its Complications Jul.-Aug. 2008, (200807), vol. 22, No. 4, ISSN 1873-460X, pp. 241-245, XP002721925 [Y] 1-17 * Venlafaxine HCl is effective in the treatment of peripheral diabetic neuropathic pain *.
Kerba, et al. Oct. 2010, Journal of Clinical Oncology, vol. 28, No. 33, pp. 4892-4897.
Kest, et. al., Pharmacology Biochemistry, and Behavior, 1995, Pergamon, vol. 52, No. 1, pp. 175-178.
Khouzam, H. R., et al., "Remission of Cancer Chemotherapy-Induces Emesis During Antidepressant Therapy with Nefazodone", Psychosomatic Medicine, 1998, vol. 60, pp. 89-91.
Kim, et al., "Activation of the spinal sigma-1 receptor enhances NMDA- induced pain via PKC- and PKA-dependent phosphorylation of the NRI subunit in mice", Br. J. Pharmacal ., 2008, vol. 154, pp. 1125-1134.
Kim, et al., Int Neurourol J.; Mar. 2016; 20(1); 13-17.
Kirchmair, R., et al., "Therapeutic Angiogenesis Inhibits or Rescues Chemotherapy-induced Peripheral Neuropathy: Taxol- and Thalidomide-induced Injury of Vasa Nervorum is Ameliorated by VEGF," Molecular Therapy, 2007, vol. 151 No. 1, pp. 69-75.
Koralewski, p., et al., Effectiveness of cyproheptadine in the management of delayed vomiting after cisplatin-based chemotherapy and the assessment of the influence of cyproheptadine on quality of lifen, Chemotherapy Dept. Rydygier Memorial Hospital, Cracow, Poland, vol. 5, pp. 499-503.
Kranz, H., et al., "Drug Release from MCC- and carrageenan-based pellets: Experiment and theory,"European Journal of Pharmaceutics and Biopharmaceutics, 2009, vol. 73, pp. 302-309.
Kuloor, et. al., Age and Aging, 2006, Oxford University Press, vol. 35, pp. 639-640.
Kunz, N. R., et al., "Diabetic neuropathic pain management with venlafaxine extended release", European Neuropsychopharmacology, Elsevier Science Publishers BV, Amsterdam, NL, vol. 10, ISSN 0924-977X, (20000901), p. 389, (20000901), XP027389705 [Y] 1-17. *Venlafaxine controlled release is effective in the treatment of pain *.
Kuruvilla et al., Arch Otolaryngol Head Neck Surg. Jan. 2009; 135(1 ): 101 -105.
Laboratoire Roger Bellon's CAS: 87: 5959, 1977.
LaBuda, et al., (2005) Pharmacological evaluation of the selective spinal nerve ligation model of neuroFathic pain in the rat. J. Neurosci. Methods 144 (2) : 175-181.
LaBudde, et al., "The Synthesis of the Mono- and Dihydroxy Derivatives of 1,2,5,6-Dibenzanthracene Excreted by the Rabbit and of Other Hydroxylated Dibenzanthracene Derivatives", J. Am. Chern. Soc., 80, pp. 1225-1236, 1958.
Lagna, et al., "Generation and phenotypic analysis of sigma receptor type I (σ1) knowckout mice," European Journal of Neuroscience, 2003, vol. 18, pp. 2188-2196.
Laird, J., et al., "Deficits in visceral pain and referred hyperalgesia in Nav1.8 (SNS/PN3)-null mice", The Journal of Neuroscience, 22(19), Oct. 1, 2002, pp. 8352-8356.
Lang, M., et al., "The Use of Polymer Heteronuclei for Crystalline Polymorph selection,"Journal of the American Chemical Society, 2002, vol. 124, No. 50, pp. 14834-14835, SI-S2.
Lau, et al. ( 2010) Electroacupuncture versus celecoxib for neuropathic pain in rat SNL model. Neuroscience 170 (2): 655-661.
Le Bars, D., et al., Animal models of nociception. *Pharmacal. Rev.*2001; 53, 597-652.
Lee, S., et al., "Large-Scale Aspects of Salt Formation: Processing of Intermediates and Final Products", Handbook of Pharmaceutical Salts: Properties, Selection, and use, 2002, Chapter 8, pp. 191-192, 211-214, Chapter 12, 265-266, 282-283.
Li, et al "Asymmetric Total Synthesis and Formal Total Synthesis of the Antitumor Sesquiterpenoid (+)-Eremantholide A", Organic Letters, vol. 9, No. 7, pp. 1267-1270, 2007.
Li, et al.,"Synthesis and Structure-Antitumor Activity of 4,6-Diamino-1 ,2-Dihydro-2,2-Dimethyi-1- (Substituted Naphthyi-2)-1,3,5-Triazines", Chern. Res. Chinese Univ., 7(3), pp. 197-200, 1991.
Li, F.,et al.,"Taurine reverses neurological and neurovascular deficits in Zucker diabetic fatty rats," Neurobiology of Disease, vol. 22, 2006, pp. 669-676.
Lippincott's Illustrated Review: Pharmacology, Richard Harvey, 5th, edition published by Wolters Kluwer "Gastrointestinal and Antiemetic Drugs", pp. 351-362.
Lowry, et al., "Protein measurement with the folin phenol reagent," J. Bio.Chem, 1951, vol. 193, pp. 265-275.
Luger N.M., et al., "Efficacy of systemic morphine suggests a fundarnen tal difference in the mechanisms that generate bone cancer vs. inflammatory pain", Pain 2002, vol. 99, pp. 397-406.
Lugar, N.M., et al., "Bone Cancer Pain: From Model to Mechanism to Therapy", J. Pain and Symp. Manag. 2005, vol. 29 pp. 832-846.
Luedtke, R. R., et al., "Neuroprotective effects of high affinity Sigma 1 receptor selective compounds," Brain Res. Mar. 2, 2012;1441:17-26.
Mantyh, "Bone cancer pain: From mechanism to therapy", Opin. Support. Palliat. Care, 2014, vol. 8, pp. 83-90.
Mar. 1, 2016 Fourth Office Action, issued in connection with Chinese Patent Application No. 201180065232 .X, including English language translation.
Mar. 29, 2016 Office Action, issued in connection with Japanese Patent Application No. 2013-541369, including English translation.
Marks, D.M., et al., "Serotonin-Norepinephrine reuptake inhibitors for pain control: Premise andpromise", Current Neuropharmacology, 2009, 7, pp. 331-336.
Maryanoff, B.E., et al., The Wittig Olefination Reaction and Modifications Involving Phosphoryl-Stabilized Carbanions. Stereochemistry, Mechanism, and Selected Synthetic Aspectsu, Chern. Rev., 1989, vol. 89, pp. 863-927.
Matsumoto RR1, Pouw B. Correlation between neuroleptic binding to sigma(1) and sigma(2) receptors and acute dystonic reactions. Eur J. Phamacol. Aug. 4, 2000;401(2) :155-60.
Maurice, T., Su, T. P., The pharmacology ofSigma-1 receptors. *Pharmacal. Ther.*2009; 124, 195-206.
McGill, J.B., et al.,"13-Biocker use and diabetes symptom score: results from the GEMINI study", Diabetes, Obesity and Metabolism, vol. 9, No. 3, May 2007, pp. 408-417.
Mega, et al., Experimental Diabetes Research, Jan. 12, 2011, Diabetic Nephropathy Amelioration by a Low-Dose Sitagliptin in an Animal Model of Type 2 Diabetes (Zucker Diabetic Fatty Rat).
Mei, et al., "Receptor Modulation of Opioid Analgesia in the Mouse", J. Pharmacol Exp. Ther.; 2002; 300(4); pp. 1070-1074.
Menten, J., "Co-analgesics and adjuvant medication in opioid treated cancer pain", Eur. J. Cancer Supplement 2005, vol. 3, pp. 77-86.
Mielke, s. et al., "Peripheral neuropathy: a persisting challenge in paclitaxel-based regimes" / European Journal of Cancer, 2006, vol. 42, pp. 24-30.
Ming, L.C., "Screening Polymorphic Forms of Drug Substances by Using Generalized Crystallization Techniques," May 2007 (English language Translation of Abstract).
Moncada A., et al., Effects of serine/threonine protein phosphatase inhibitors on morphine-induced antinociception in the tail flick test in mice. *Eur J Pharmacal.*2003; Mar. 28; 465(1-2): 53-60.
Mosandl, et al., "Stereoisomeric Flavor Compounds XLIV: Enantioselective Analysis of Some Important Flavor Molecules", J. High Resol. Chromatog 13(9), pp. 660-662, 1990.

(56) References Cited

OTHER PUBLICATIONS

Mouedden, et al., "Pharmacological evaluation of opioid and non-opioid analgesics in a murine bone cancer model of pain", Pharm. Biochem. And Behavior, 2007, vol. 86, pp. 458-467.
Mueller, et al., "Some Derivatives of 7-Methoxy- and 10-Methoxybenzo (f) quinoline", J. Am. Chem. Soc., 66, pp. 860-862, 1944.
Mukerji, et al., "Addition of Nitrile Oxides to Olefins, Synthesis of Dihydrojasmone and Starting Material for Prostanoids. A Novel Route to Pyrroles", Tetrahedron, 39 (13) pp. 2231-2235, 1983.
Nakajima K., et al., An increase in spinal cord noradrenaline is a major contributor to the antihyperalgesic effect of antidepressants after peripheral nerve injury in the rat. Pain.2012; 153(5): 990.
Nakazato a., et al., "Synthesis and SAR of 1-alkyl-2-phenylethylamine derivatives designed from N,Ndipropyl-4-methoxy- 3-(2-phenylethoxy) phenylethylamine to discover ?1ligands", J. Med. Chem., (1999), vol. 42, pp. 3965-70.
Nausea and Vomiting (PDQ) Health Professional Version: Prevention and Managemenl of Acute or Delayed Nausea and Vomiting (Emesis). National Cancer Institute <http://www.cancer.gov/about-cancer/treatment/sideeffects/nausea/nausea-hp-pdq#sectlon/ - 66>.
Nieto, F. R., et al., "188 A New Selective Sigma-1 Receptor Antagonist (S1RA) Inhibits the Development and Expression of Neuropathic Pain Induced by Paclitaxel in Mice," European Journal of Pain Supplements, vol. 4, No. 1, 2010, p. 56.
Nieto, F.R. et al.,"Tetrodotoxin inhibits the development and expression of neuropathic pain induced by paclitaxel in mice", Pain, 2008, vol. 137, pp. 520-531.
Niiyama, et al., "SB366791, a TRPVI antagonist, potentiates analgesic effects of systemic morphine in a murine model of bone cancer pain", Br. J. Anaesth., 2009, vol. 102, pp. 251-258.
Noda, et al., "A Neuroactive Steroid, Dehydroepiandrosterone Sulfate, Attenuates the Development of Morphine Dependence: An Association with Sigma1 Receptors," Neuroscience 2001 Abstract, Presentation No. 668.4, Nov., 2001.
O'Brien, C. J., "Recycling the Waste: The Development of a Catalytic Witting Reaction", Agnew. Chern. Int. Ed. 2009, vol. 48, pp. 6836-6839.
Office Action dated Mar. 18, 2013 in connection with Russian Patent Application No. 2010138634, filed Feb. 17, 2009.
Official Action corresponding to Japanese Patent Application No. 2013-523580, dated Mar. 31, 2015.
Ohsawa, et al.,"Effect of acute topical application of(+)-pentazocine on the mechanical allodynia in diabetic mice" Eur. J. P'harmacal., 2010, 641, pp. 49-53.
Olivar, T., et al.,"Cyclophosphamide cystitis in mice: behavioural characterisation and correlation with bladder inflammation", European Journal of Pain, 3, 1999, pp. 141-149.
Oltman, C.L., et al., "Progression of vascular and neural dysfunction in sciatic nerves of Zucker diabetic fatty and Zucker rats", Am. J. Physiol. Endocrinol. Metab., vol. 289, 2005, pp. E113-E122.
Oltman, C.L., et al., "Vascular and neural dysfunction in Zucker diabetic fatty rats: a difficult condition to reverse", Diabetes, Obesity and Metabolism, vol. 10, 2008, pp. 64-74.
Oltman, et al., Treatment of Zucker diabetic fatty rats with AVE7688 improves vascular and neural dysfunction, Diabetes, Obesity and Metabolism, vol. 11, No. 3, 2009, pp. 223-233.
O'Neill, J., et al., Unravelling the rnystery of capsaicin: a tool to understand and treat pain. Pharrnacol Rev. Oct. 2012;64(4):939-71.
Ongioco, C. D., et al., Alpha2-adrenergic receptors in human dorsal root ganglia: predominance of alpha2b and alpha2c subtype mRNSs, Anesthesiology2000; 92 (4): 968-976.
Otto, et al., Pain Medicine, 2011, 12: 437-450, "Longitudinal Study of painful Diabetic Neuropathy in the Zucker Diabetic Fatty Rat Model of Type 2 Diabetes: Impaired Basal G-Protein Activity Appears to Underpin Marked Morphine Hyposensitivity at 6 Months.".
Owens, N.J. et al., "Antiemetic efficacy of prochlorperazine, haloperidol, and droperidol in cisplatin-induced emesis", Clinical Pharmacy, 1984, vol. 3, pp. 168-170.

Pacharinsak, C., et al., ' "Animal Models of Cancer Pain", Comparative Medicine, 2008, vol. 58, No. 3, pp. 220-233.
Paice, J. A., "Clinical Challenges: Chemotherapy-induced Peripheral Neuropathy", Seminars in Oncology Nursing, 2009, vol. 25, N. 2, Suppl 1, pp. S8-S19.
Palmer, J. L., and Fisch, M. J., "Association Between Symptoms Distress and Survival in Outpatients Seen in a Palliative Care Caner Center", Journal of Pain and Symptom Management, 2005, vol. 29, No. 6, pp. 565-571.
Paquette et al. in Psychopharmacology (Berlin) 204(4):743-754 (2009).
Park, S.B. et al. "Mechanisms Underlying Chemotherapy-Induced Neurotoxicity and the Potential for Neuroprotective Strategies", Current Medicinal Chemistry, 2008, vol. 15, pp. 3081-3094.
Perret, D., et al., "Targeting voltage-gated calcium channels for neuropathic pain rnanagement", Neurotherapeutics: The Journal of the American Society for Experimental NeuroTherapeutics, vol. 6, Oct. 2009, pp. 679-692.
Petrie, C. et al., "A Novel Biotinylated Adenylate Analogue Derived from Pyrazolou3,4-D 3/4 Pyrimidine for Labeling DNA Probes "Bioconjugate Chemistry, ACS, Washington, DC, US LNKD-DOI:10.1021/BC00012A011, vol. 2, No. 6, Nov. 1, 1991 (Nov. 1, 1991) , pp. 441-446, XP0005727891SSN: 1043-1802.
Polomano, R.C. , et al., "Chemotherapy-evoked Painful Peripheral Neuropathy", Pain Medicine, 2001, vol. 2, No. 1, pp. 8-14.
Polomano, R.C., et al., "Pain and neuropathy in cancer survivors: Surgery, radiation, and chemotherapy can cause pain; research could improve its detection and treatment", Cancer Nursing, Lippincott-Raven Pub., Hagerstown, MD, US, (20060301), vol. 29, No. 2, suppl, ISSN 0162-220X, pp. 39-47, XP009107315 [A] 1-16 * p. 41, col. R, paragraph 2 ** p. 42, col. R, paragraph 2 *.
Poncelet, A.N., "Risk factors, patterns of presentation, diagnosis, and treatment", Geriatrics, vol. 58, No. 6, Jun. 2003, pp. 16-18, 24-30.
Postma, T.J., et al., "Paclitaxel-induced neuropathy," Annals of Oncology, 1995, vol. 6, pp. 489- 494.
Price, et al., J. Am. Chem. Soc., (2005), vol. 127, p. 5512.
Prodrug [online], [retrieved on Mar. 11, 2007. Retrieved from the Internet, URL; http://en.wikipedia.org/wiki/Prodruq>.
Puente, B., et al., "Sigma-1 receptors regulate activity-21 induced spinal sensitization and neuropathic pain after peripheral nerve injury", Pain, 2009, vol. 145, pp. 294-303.
Puskas, F., et al., Intrathecal clonidine and severe hypotension after cardiopulmonary bypass, Anesth Analg.2003; 97 (5): 1251-1253.
Quasthoff, S., et al., "Chemotherapy-induced peripheral neuropathy," J Neural., 2002, vol. 249, pp. 9-17.
Radesca, et al., "Synthesis and Receptor Binding of Enantimeric N-Substituted cis-N-[2(3,4 Dishlorophenyl)ethyl]-2-(1-pyrrolidinyl)cyclohexylamines as High-Affinity σReceptor Ligands," J. Med. Chem., 1991, vol. 34, pp. 3058-3065.
Rao, R.D., et al., "Efficacy of Lamotrigine in the Management of Chemotherapy-induced Peripheral Neuropathy placebo-controlled trial, N01C3", Cancer; 2008, 112(12), 2802-2808.
Raynov, J., "Antiemetics: Side effects and reactions", Archive of Oncology, 2001, vol. 9, No. 3, pp. 151-153.
Receveur, Jean-Marie, et al., "Synthesis and biological evaluation of conformationally restricted gabapentin analogues", Bioorganic & Medicinal Chemistry Letters, 9, 1999, pp. 2329-2334.
Reuben, S. S., et al., "Evaluation of efficacy of the perioperative administration of venlafaxine XR in the prevention of postrnastectorny pain syndrome", Journal of Pain and Syrnptom Management, Feb. 2004, vol. 27, No. 2, pp. 133-139.
Rodriguez-Spong, B., et al., "General principles of pharmaceutical solid polymorphism: a supramolecular Perspective," Advanced Drug Delivery Reviews, vol. 56 (2004) pp. 241-274.
Roh, D., et al., "Intrathecal Injection of the 01 Receptor Antagonist BD1047 Blocks Both Mechanical Allodynia and Increases in Spinal NR1 Expression during the Induction Phase of Rodent Neuropathic Pain", Anesthesiology, 2008, vol. 109, No. 5, pp. 879-889.
Roila, F., et al., "Delayed emesis: moderately emetogenic chemotherapy", Support Care Cancer, 2005, vol. 13, pp. 104-108.

(56) References Cited

OTHER PUBLICATIONS

Romero, L., et al., J. Pharmacological properties of SIRA, a new Sigma-1 receptor antagonist that inhibits neuropathic pain and activity-induced spinal sensitization. Br. J. Pharmacal.2012; doi: 10.1111/j.1476-5381.
Roos, et al., Radiotherapy and Oncology, 2003, vol. 67, pp. 207-212.
Rossiter, et al., "Copper (H)-Mediated Arylation with Aryl Boronic Acids for the N-Derivatization ofPyrazole Libraries," J. Comb. Chern., 2004, vol. 6, pp. 385-390, published on web Feb. 5, 2004.
Rouleau, a., et al., "Anti-inflammatory and antinociceptive properites of BP 2-94, a histamine H3-receptor agonist prodrug", The Journal of Pharmacology and Experimental Therapeutics, vol. 295, No. 1, 2000, pp. 219-225.
Rowinsky, E.K. et al., "Phase I and Pharmacologic Study of Paclitaxel and Cisplatin with Granulocyte Colony-25 Stimulating Factor: Neuromuscular Toxicity is Dose-Limiting", Journal of Clinical Oncology, 1993, vol. 11, No. 10, pp. 2010-2020.
Rowinsky, E.K., et al., "Clinical Toxicities Encountered 24 with Paclitaxel (TAXOL) ", Seminars in Oncology, 1993, vol. 20, No. 4, suppl. 3, pp. 1-15.
Sabetkasaie, M., et al., "Clonidine and guanfacine-induced antinociception in visceral pain: possible role of alpha2/I2 binding sites", European Journal of Pharmacology, Elsevier Science, NL, vol. 501, No. 1-3, doi:10.1016/J.EJPHAR.2004.08.010, ISSN 0014-2999, pp. 95-101,.
Said, G., "Diabetic Neuropathy", Proceedings advanced studies in Medicine, vol. 1, No. 11, Dec. 2001, pp. 457-459.
Sakurada T., et al., Differential effects of intraplantar capsazepine and ruthenium red on capsaicin-induced desensitization in mice. Pharmacal Biochern Behav. Apr. 2003; 7 5 (1): 1 15-21.
Sampson, C., et al., "Effects of imidazoline I2 receptor ligands on acute nociception in rats." Neuroreport Jan. 25, 2012, (Jan. 25, 2012), vol. 23, No. 2, ISSN 1473-558X, pp. 73-77, XP009169909 [Y] 1-15 * See abstract: imidazoline I2 receptor ligands have antinociceptive effect in acute pain *.
Samso, E., et al., Comparative assessment of the anaesthetic and analgesic effects of intramuscular and epidural clonidine in humans, Can J Anaesth.1996; 43 (12): 1195-1202.
Sanchez-Fernandez, C., et al., "Potentiation of morphine-induced mechanical antinociception by sigma-1 receptor inhibition: role of peripheral sigma-1 receptors", Neuropharmacology, 70, 2013, pp. 348-358.
Sant et al., "The mast cell in interstitial cystitis: role in pathophysiology and pathogenesis,"Urology, 69, Suppl 4A, 2007, pp. 34-40.
Schetz et al. in Brain Research 1181 (2007) 1-9.
Schiff, et al., Nature vol. 277 pp. 665-667. Publication date: Feb. 22, 1979.
Schlegel, T., et al., "Responsiveness of C-fiber nociceptors to punctate force-controlled stimuli in isolated rat skin: lack of modulation by inflammatory mediators and flurbiprofen" Neuroscience Letters, vol. 361, 2004, pp. 163-167.
Hanner et al., "Purification, molecular cloning, and expression of the mammalian sigma1-binding site," Proc. Natl. Acad. Sci. USAvol. 93, pp. 8072-8077, Jul. 1996 Pharmacology.
Schoeffter, et al., "Functional, endogenously expressed 5-hydroxytryptamine 5-ht7 receptors in human vascular smooth muscle cells," British Journal of Pharmacology, 1996, vol. 117, pp. 993-994.
Schreiber, S., et al., "The antinociceptive effect of venlafaxine in mice is mediated through opioid and adrenergic mechanisms", Neuroscience Letters, Limerick, IE, vol. 273, doi: 10.1016/S0304-3940(99)00627-8, ISSN 0304-3940, pp. 85-88, XP003009174 [Y] 1-17 * Venlafaxine has antinociceptive effects and is effective for treating pain. *.
Seigel, L.J., et al., The Control of Chemotherapy-Induced Emesis, Ann Intern Med. 1981;95(3) :352-359.

Selwood, D. L., et al. Synthesis and Biological Evaluation of Novel Pyrazoles and lndazoles as Activators of the Nitric Oxide Receptor, Soluble Guanylate Cyclase, J. Med. Chern, 2001, vol. 44,pp. 78-93.
Gotub et al., "Molecular Classification of Cancer: Class Discovery and Class Prediction by Gene Expression Monitoring," Science, 286: 531-537, 1999.
Sevcik, M.A., et al., "Jlnti-NGF therapy profoundly reduces bone cancer pain and the accompanying increase in markers of peripheral and central sensitization", Pain 2005, vol. 115, pp. 128-141.
Shaw, et al., Proc. Soc. Exp. Biol. Med., (1983), vol. 173, No. 1, pp. 68-75.
Shen, D.M., et al., "Versatile and Efficient Solid-Phase Syntheses of Pyrazoles and Isoxazoles", Organic Letters, 2000, vol. 2, No. 18, pp. 2789-2792.
Shimizu, I., et al., "Effects of Ah-9700, (+)-pentazocine, DTG and oxybutynin on micturition in anesthetized rats with acetone-induced cystitis", Life Sciences 69,2001, pp. 1691-1697.
Shimoyama, E., et al., Integrative Medicine you Need to know now "Cancer and Integrative Medicine Palliative Medicine", Modern Physician, Nov. 2008, vol. 28, No. 11, pp. 1605-1607 [inc. machine English language translation].
Shu, et al., "Parameter Effects on the Thermal Reaction of Cystine and 2,5-Dimethyl-4-hydroxy-3(2H)-furanone", ACS Symposium Letters, 409, pp. 229-241, 1989.
Shvidenko, K.V., et al., "Recyclization Reactions of 2-(1-Benzoylpyrrolidin- 2-Ylidene)Malononitrile", 2010, vol. 46, No. 1, pp. 56-60.
Siau, C., et al., "Dysregulation of Cellular Calcitt.rn Homeostasis in Chemotherapy-Evoked Painful Peripheral Neuropathy", Anest:h Analg., 2006, 102(5), pp. 1485-1490.
Sierralta, F., et al., Alpha-Adrenoceptor and opioid receptor modulation of clonidine-induced antinociception, Br J Pharmacal.1996; 119 (3): 551-554.
Silvey et al. In Journal of Clinical Oncology 6(9), 1397-1400 (1988) (Abstract).
Sima, A.A.F., "The heterogeneity of diabetic neuropathy", Frontiers in Bioscience, May 2008, pp. 4809-4816.
Sima, A.A.F., et al., "A comparison of diabetic polyneuropathy in Type II diabetic BBZDR/Wor rats and in Type I diabetic BBNVor rats", Diabetologia, vol. 43, 2000, pp. 786-793.
Smith, et al., Life Sci., (2004), vol. 74, No. 21, pp. 2593-604.
Smith, J. C. et al., "Haloperidol: An alternative butyrophenone for nausea and vomiting prophylaxis in anesthesia," AANA Journal 2005, vol. 73, No. 41 pp. 273-275.
Snyder, et al., "Receptor Mechanisms in Antipsychotic Drug Action: Focus on Sigma Receptors," Journal of Neuropsychiatry, Winter 1989, Vol , No. 1, pp. 7-15.
Sonal, G., et al., Ther. Adv. Urol., (2011), vol. 3, No. 1, pp. 19-33.
Souillac, et al., Characterization of Delivery Systems, Differential Scanning Calorimetry, pp. 217-218 (in Encyclopedia of Controlled Drug Delivery, 1999, John Wiley & Sons, pp. 212-227.
Stahl, P.H., et al., "Monographs on Acids and Bases", Handbook of Pharmaceutical Salts: Properties, Selection, and Use, 2002, pp. 265-266, 282-283.
Non-Final Office Action dated Feb. 2, 2009 in related application U.S. Appl. No. 11/574,361 citing STN-search report report JP10055048 (p. 8).
Strupp, et al., "Transdermal fentanyl during high-dose chemotherapy and autologous stem cell support" (2000) Oncology Reports, 7:659-661.
Stubblefield, et al., "Upper-Extremity Pain Disorders in Breast Cancer" (2006) Arch Phys Med Rehabil, vol. 87, Suppl 1, pp. S96-S99.
Su, et al., Pharmacology & Therapeutics, vol. 124, pp. 195-206, 2009.
Sussman, N., "SNRis versus SSRis: Mechanisms of action in treating depression and painful physical symptoms", Primary Care Companion J. Clin. Psychiatry, 2003, 5 (suppl 7), pp. 19-26.
Suzuki, Y., et al., "Lowered response threshold and increased responsiveness to mechanical stimulation of cutaneous nociceptive fibers in streptozotocin-diabetic rat skin in vitro—correlates of mechanical allodynia and hyperalgesia observed in the early stage of diabetes", Neuroscience Research, vol. 43, 2002, pp. 171-178.

(56) References Cited

OTHER PUBLICATIONS

Tanda, S., et al., "Pains Resistant to Opioids, and Countermeasures thereof~Including Peripheral Neuropathy Measures of Oxaliplatin", Pharmacy, Oct. 2007, vol. 58, No. 11, pp. 2947-2953 [inc. machine English language translation].

Taylor, C.P., "Mechanisms of analgesia by gabapentin and pregabalin- calcium channel alpha2-delta [Ca v alpha2-delta]ligands", Pain, 142, 2009, pp. 13-16.

Telleria-Diaz, et al., Pain, 2010, 148, pp. 26-35.

Theoharides, T.C., "Mast cell involvement in interstitial cystitis: a review of human experimental evidence," Urology, (2001), vol. 57, No. 6, pp. 47-55.

Tietze, L., et al., Synthesis, (11), 1079-1080, 1993.

Tramer, M. R., et al., "Efficacy and Adverse Effects of Prophylactic Anti emetics during Patient-Controlled Analgesia Therapy: A Quantitative Systematic Review, "Anesth. Analg., 1999, vol. 88, pp. 1354-1361.

Tyers et al. Oncology 49(4), 263-268 (1992) (Abstract).

Uchitel, O.D., et al., "Acute modulation of calcium currents and synaptic transmission by Gabapentinoids," Channels, 4:6, Nov./Dec. 2010, pp. 490-496.

Van De Merwe, J.P., et al., "Diagnostic criteria, classification, and nomenclature for painful bladder syndrome/interstitial cystitis: an ESSIG proposal", European Urology, 53, 2008, pp. 60-67.

Van Sickle et al. Gastroenterology 121 (4), 767-774 (2001) (Abstract).

Vedejs, E., "Stereochemistry and Mechanism in the Wittig Reaction," Topics in Stereochemistry, 1994, vol. 21, pp. 1-157.

Velucci, "Heterogeneity of Chronic Pain", Clin. Drug Invest. 2012, 32 Suppl. 1, pp. 3-10.

Venturello, C., "2-Arylazo-2, 5-dimethyl-3-oxo-2, 3-dihydrof urans, useful intermediates in the synthesis of 1-aryl-5-methyl-3-pyrazolones", Synthesis, 1979, pp. 283-287.

Venturello, C., et al., "A Novel Synthesis of Pyrazol-3-ones Form Biacetyl Dimer and Arenediazonium Salts", Journal of the Chemical Society, Perkin Transactions 1: Organic and Bio-organic Chemistry, (1972-1999), 7, 681-685, 1978.

Vileikyte, L., et al., Psychological aspects of diabetic neuropathic foot complications: an overview, Diabetes/Metabolism Research and Reviews, 2004, vol. 20 (Suppl1), pp. S13-S18.

Vinik, A., et al., Nature Clinical Practice Endocrinology & Metabolism, (2006), vol. 2, pp. 2-13.

Vippagunta, et al., Crystalline solids, Advanced Drug Delivery Reviews, 48: 1-26, 2001.

Virmani, et al., Indian Journal of Chemistry, Section B:Organic Chemistry Including Medicinal Chemistry,vol. 17, 1979, pp. 472-477.

Virmani, V. et al., "Methyl-{3-[5-(4-nitro-phenyl)-1-phenyl-1H-pyrazol-3-yl]propyl}-amine", Database Beilstein, Beilstein Institute for Organic Chemistry, Frankfurt-Main, DE, Database accession No. 705147, XP002605613 [X] 1-3,9 * the whole document *.

Virmani, V. et al., "Methyl-{4-[5-(4-nitro-phenyl)-1-phenyl-1H-pyrazol-3-yl]-butyl}amine", Database Beilstein, Beilstein Institute for Organic Chemistry, Frankfurt-Main, DE, Database accession No. 706821, XP002605614 [X] 1-3,9 * the whole document *.

Virmani, V. et al., "Methyl-{5-[5-(4-nitro-phenyl)-1-phenyl-1H-pyrazol-3-yl]-pentyl}-amine", Database Beilstein, Beilstein Institute for Organic Chemistry, Frankfurt-Main, DE, Database accession No. 710983, XP002605615 [X] 1-3,9 * the whole document *.

Vorobeychik, et al., "Combination Therapy for Neuropathic Pain—A Review of Current Evidence," CNS Drugs, 2011, pp. 1-12.

Wagaw, S. et al., "A Palladium-Catalyzed Strategy for the Preparation of Indoles: A Novel Entry Into the Fischer Indole Synthesis", J. American Chemical Society, 1998, vol. 120, pp. 6621-6622.

Walker, et al., "Sigma Receptors: Biology and Function," Pharmacological Review, 1990, vol. 42, No. 4, pp. 355-402.

Wantuch, C., et al., "Pharmacological validation of a model of cystitis pain in the mouse", Neuroscience Letters, 421, 2007, pp. 250-252.

Wasserheit, C., et al., "Phase II trial of paclitaxel and cisplatin in women with advanced breast cancer: an active regimen with limiting neurotoxicity", Journal of Clinical Oncology, 1996, vol. 14, No. 7 pp. 1993-1999.

Weetman, A.P., "Graves' hyperthyroidism: how long should antithyroid drug therapy be continued to achieve remission?," Nature Clinical Practice Endocrinology and Metabolism, vol. 2, No. 1, Jan. 2006, pp. 2-3.

Werling, L.L. et al., "A comparison of the binding profiles of dextromethorphan, memantine, fluoxotinc and amitriptyline: treatment of involuntary emotional expression disorder," Exp Neurol. Oct. 2007;207 (2):248-57.

Wickham, "Chemotherapy-Induced Peripheral Neuropathy: A Review and Implications for Oncology Nursing Practice" (2007) Clinical Journal of Oncology Nursing, vol. 11, No. 3, pp. 361-376.

Wild, S., et al., "Global Prevalence of Diabetes", Diabetes Care, vol. 27, No. 5, May 2004, pp. 1047-1053.

Wilkes, G. "Peripheral Neuropathy Related to Chemotherapy", Seminars in Oncology Nursing, 2007, vol. 23, 3. pp. 162-173.

Wilson, S. G., "The heritability of antinociception: common pharmacogenetic mediation of five neurochemically distinct analgesics," *J Pharmacal Exp Ther.*2003; 304 (2): 547-559.

Winkler, et al., "Synthesis of Highly Functionalized Furanones via Aldol Reaction of 3-Silyloxyfurans", Organic Letters, vol. 7, No. 3, pp. 387-389, 2005.

Wolf, S., et al., "Chemotherapy-induced peripheral neuropathy: Prevention and treatment strategies, " European Journal of Cancer, 2008, vol. 44, issue 1|, pp. 1507-1515.

Wu, et al., Regulatory Perspectives of Type II Prodrug Development and Time- Dependent Toxicity Management: Nonclinical Pharm/Tox Analysis and the Role of Comparative Toxicology, Toxicology, 236: 1-6, 2007.

Wunsch, et al., Journal Med. Chem. vol. 55, No. 19, pp. 8209-8210, 2012.

Xiaoping, et al., "Involvement of the spinal NMDA receptor/PKCy signaling 12 pathway in the development of bone cancer pain", Brain Research, 2010, vol. 1335, pp. 83-90.

Xu, J. et al., Identification of the PGRMCI protein complex as the putativP. sigrna-2 receptor binding site. Nat Comnun. Jul. 5, 2011; 2:380.

Yaksh, T. L., Pharmacology of spinal adrenergic systems which modulate spinal nociceptive processing. *Pharmacal Biochem Behav.*1985; 22(5): 845-58.

Yeretzian, et al., "Analysing the headspace of coffee by proton-transfer-reaction mass-spectrometry", Int J. Mass Spect, 223-224 (1-3), pp. 115-139, 2003.

Zhang et al. in Synapse 15(4):276-284 (1993), Abstract.

Zheng, F.Y., et al. "The Response of Spinal Microglia to Chemotherapy Evoked Painful Peripheral Neuropathies Is Distinct From That Evoked by Traumatic Nerve Injuries," *Neuroscience*, 2011, 176, pp. 447-454.

Gonzalez-Cano, R. et al., "Sigma 1 Receptors are Involved in the Visceral Pain Induced by Intracolonic Administration of Capsaicin in Mice," Anesthesiology, Mar. 2013, vol. 118(3), pp. 691-700.

* cited by examiner

1-ARYL-3-AMINOALKOXY PYRAZOLES AS SIGMA LIGANDS ENHANCING ANALGESIC EFFECT OF OPIOIDS AND ATTENUATING THE DEPENDENCY THEREOF

CROSS-REFERENCE TO RELATED APPLICATIONS

This application is a Continuation of U.S. patent application Ser. No. 12/988,951, filed Oct. 12, 2010, which is the National Stage of International Application No. PCT/EP09/054974, filed Apr. 24, 2009, which claims benefit of European Application. No. 08380122.5, filed Apr. 25, 2008, the contents of all of which are incorporated by reference herein.

FIELD OF THE INVENTION

The present invention relates to potentiation of the analgesic effect of opioids and opiates as well as to attenuation of the addiction thereof. More specifically, the present invention relates to the use of a group of sigma receptor ligands for the potentiation of the analgesic effect of opioids and opiates and for decreasing the dependency induced by them at the same time.

BACKGROUND OF THE INVENTION

Opioids and opiates are potent analgesics widely used in clinical practice. Opioid and opiates drugs are classified typically by their binding selectivity in respect of the cellular and differentiated tissue receptors to which specific drug specie binds as a ligand. These receptors include mu ($\mu$), delta ($\delta$), kappa ($\kappa$) and the nociceptive receptors.

The well-known narcotic opiates, such as morphine and its analogues, are selective for the opioid mu receptors. Mu receptors mediate analgesia, respiratory depression, and inhibition of gastrointestinal transit. Kappa receptors mediate analgesia and sedation. However, despite their good activity as analgesics, opioids and opiates have the drawback of causing dependence.

Sigma receptors are non-opiaceous type of receptors of great interest in pharmacology due to their role in analgesia related processes. The sigma binding sites have preferential affinity for the dextrorotatory isomers of certain opiate benzomorphans, such as (+)SKF 10047, (+)cyclazocine, and (+)pentazocine and also for some narcoleptics such as haloperidol. The sigma receptor has at least two subtypes, which may be discriminated by stereoselective isomers of these pharmacoactive drugs. SKF 10047 has nanomolar affinity for the sigma 1 ($\sigma$-1) site, and has micromolar affinity for the sigma 2 ($\sigma$-2) site. Haloperidol has similar affinities for both subtypes.

It has been reported that some sigma ligands in combination with opioids or opiates are capable of modulating the analgesic effect thereof. It is known, for example, that haloperidol potentiates the activity of different opioids and opiates such as morphine, DADL or bremazocine [Chichenkov, O. N. et al: Effect of haloperidol on the analgesic activity of intracisternally and intrathecally injected opiate agonists, *Farmakologiya i Toksikologiya* (Moscow) (1985), 48(4), 58-61]. Chien C. et al also referred the synergistic effect of the combination of haloperidol and morphine [Selective antagonism of opioid analgesia by a sigma system, *J Pharmacol Exp Ther* (1994), 271, 1583-1590 and Sigma antagonists potentiate opioid analgesia in rats, *Neurosci Lett* (1995), 190, 137-139] and Marazzo A. et al taught the capacity of the sigma ligand (+)-MR200 to modulate $\kappa$-opioid receptor mediated analgesia. Mei J. et al confirmed the importance of sigma-1 receptors as a modulatory system on the analgesic activity of opioid drugs [Sigma1 receptor modulation of opioid analgesia in the mouse, *J Pharmacol Exp Ther* (2002), 300(3), 1070-1074]. Notwithstanding, in all of this cases the problem of dependence induced by opioids and opiates remain to be present.

One of the pharmacological approaches to solve the problem of opioid and opiate dependency has been the co-administration of opioids or opiates and sigma ligands. For instance, sigma-1 receptor agonist SA4503 has been shown to have a modulatory effect on addiction to morphine [Nomura, M. et al: Studies on drug dependence (Rept. 322) : Attenuation of morphine- and psychostimulants-induced place preference by sigma1 receptor agonist SA4503, 72nd *Annual Meeting of the Japanese Pharmacological Society* (Sapporo, Japan-March 1999)]. Also, sigma-1 agonist DHEA has shown some capacity to attenuate the development of morphine dependence [Noda, Y. et al: A neuroactive steroid, dehydroepiandrosterone sulfate, attenuates the development of morphine dependence: an association with sigma1 receptors, $31^{st}$ *Annual Meeting of the Society of Neuroscience* (San Diego-November 2001)]. EP1130018 teaches the use of sigma ligands for the treatment of drug addiction to morphine, cocaine and methamphetamine. However, none of these approaches show an enhancement of the analgesic effect of morphine.

Therefore, it is desirable to find sigma ligands capable of synergistically potentiate the analgesic effect of opioids or opiates while attenuating at the same time the dependency thereof.

SUMMARY OF THE INVENTION

The inventors of the present invention have surprisingly found that some specific sigma ligands show the capacity to potentiate synergistically the analgesic effects of opioids or opiates while decreasing at the same time the dependency induced by them.

One objective of the present invention relates to a combination of at least one sigma ligand and at least an opioid or opiate compound wherein the sigma ligand has the general formula (I):

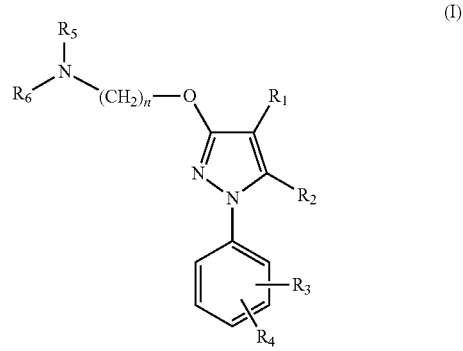

wherein
 $R_1$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_8$, —$C(O)OR_8$, —$C(O)NR_8R_9$ —$C\!=\!NR_8$, —CN, —$OR_8$, —$OC(O)R_8$, —$S(O)_t$—$R_8$, —$NR_8R_9$, —$NR_8C(O)R_9$, —$NO_2$, —$N\!=\!CR_8R_9$, or halogen;

$R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$ —$C\!=\!NR_8$, —CN, —$OR_B$, —$OC(O)R_8$, —$S(O)_t$—$R_8$, —$NR_8R_9$, —$NR_8C(O)R_9$, —$NO_2$, —$N\!=\!CR_8R_9$, or halogen;

$R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$ —$C\!=\!NR_8$, —CN, —$OR_8$, —$OC(O)R_8$, —$S(O)_tR_8$, —$NR_8R_9$, —$NR_8C(O)R_9$, —NO2, —$N\!=\!CR_8R_9$, or halogen, or together they form a fused ring system;

$R_5$ and $R_6$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_S$, —$C(O)OR_8$, —$C(O)NR_8R_9$ —$C\!=\!NR_8$, —CN, —$OR_8$, —$OC(O)R_8$, —$S(O)_tR_8$, —$NR_8R_9$, —$NR_8C(O)R_9$, —$NO_2$, —$N\!=\!CR_8R_9$, or halogen, or together form, with the nitrogen atom to which they are attached, a substituted or unsubstituted heterocyclyl group;

n is selected from 1, 2, 3, 4, 5, 6, 7 or 8;

t is 1,2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;

or a pharmaceutically acceptable salt, isomer, prodrug or solvate thereof.

Another objective of this invention refers to the simultaneous, separate or sequential administration of a combination as defined above to potentiate the analgesic effect of an opioid or opiate and/or decrease its dependency.

DETAILED DESCRIPTION OF THE INVENTION

Figure 1:
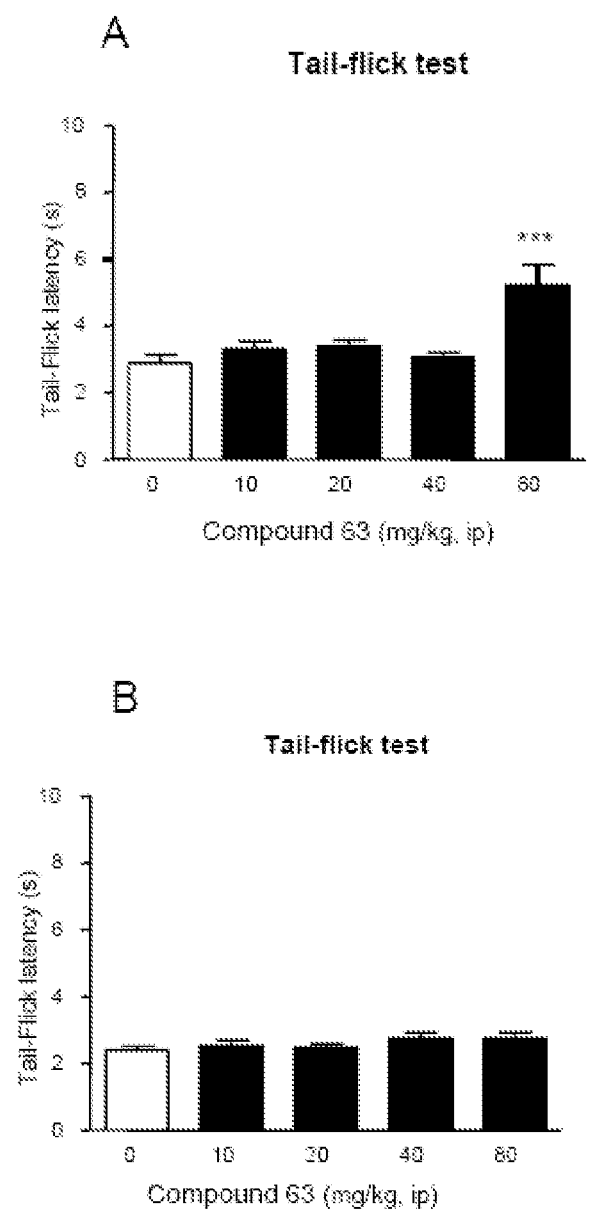
FIG. 1: Dose-response effects of acute administration of compound 63 (10, 20, 40 and 80 mg/kg, i.p.) in the tail-flick test in male CD-1 WT mice (A) and in CD-1 σ1R-KO mice (B). Compounds were injected 30 min before the test. Data, obtained from 12 (A) or 10 (B) animals per group, are presented as the mean±SEM of the tail-flick latency (s). ***$p<0.001$ vs. vehicle (HPMC 0.5%) treated group (Newman-Keuls Multiple comparison Test post-ANOVA).

The compounds of formula (I) can be prepared as disclosed in our previous application WO2006021462.

Thee term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are preferred particularly, as well as those formed with ammonium cations ($NH_4$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate.

Any compound that is a prodrug of a compound of formula I is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

In a preferred embodiment, $R_1$ in compounds of formula I is selected from H, —$COR_8$, or substituted or unsubstituted alkyl. More preferably, $R_1$ is elected from H methyl of acetyl. A more preferred embodiment is when $R_1$ is H.

In another preferred embodiment, $R_2$ represents H or alkyl, more preferably methyl.

In yet another preferred embodiment of the invention, $R_3$ and $R_4$ are situated in the meta and para positions of the phenyl group, and preferably, they are selected independently from halogen or substituted or unsubstituted alkyl.

In an especially preferred embodiment of the invention, both $R_3$ and $R_4$ together with the phenyl group form a fused ring system, more preferably, a naphthyl ring system.

Also, embodiments where n is selected from 2, 3, 4 are preferred in the context of the present invention.

Finally, in another embodiment it is preferred that $R_5$ and $R_6$ together form a morpholine-4-yl group.

In preferred variants of the invention, it encompasses the combination of at least one opioid or opiate with at least one compound of formula I selected from:

[1] 4-{2-[1-(3,4-dichlorophenyl)-5-methyl-1H-pyrazol-3-yloxy)ethyl}morpholine
[2] 2-[1-(3,4-Dichlorophenyl)-5-methyl-1H-pyrazol-3-yloxy]—N,N-diethylethanamine
[3] 1-(3,4-Dichlorophenyl)-5-methyl-3-[2-(pyrrolidin-1-yl)ethoxy]-1H-pyrazole
[4] 1-(3,4-Dichlorophenyl)-5-methyl--3-[3-(pyrrolidin-1-yl)propoxy]-1H-pyrazole
[5] 1-{2-[1-(3,4-Dichlorophenyl)-5-methyl-1H-pyrazol-3-yloxy]ethyl}piperidine
[6] 1-{2-[1-(3,4-dichlorophenyl)-5-methyl-1H-pyrazol-3-yloxy]ethyl}-1H-imidazole
[7] 3-{1-[2-(1-(3,4-Dichlorophenyl)-5-methyl-1H-pyrazol-3-yloxy)ethyl]piperidin-4-yl}-3H-imidazo[4,5-b]pyridine
[8] 1-{2-[1-(3,4-Dichlorophenyl)-5-methyl-1H-pyrazol-3-yloxy]ethyl}-4-methylpiperazine
[9] Ethyl 4-{2-[1-(3,4-dichlorophenyl)-5-methyl-1H-pyrazol-3-yloxy]ethyl}piperazine carboxylate
[10] 1-(4-(2-(1-(3,4-dichlorophenyl)-5-methyl-1H-pyrazol-3-yloxy)ethyl)piperazin-1-yl)ethanone
[11] 4-{2-[1-(4-Methoxyphenyl)-5-methyl-1H-pyrazol-3-yloxy]ethyl}morpholine
[12] 1-(4-Methoxyphenyl)-5-methyl-3[2-(pyrrolidin-1-yl)ethoxy]-1H-pyrazole
[13] 1-(4-Methoxyphenyl)-5-methyl-3-[3-(pyrrolidin-1-yl)propoxy]-1H-pyrazole
[14] 1-[2-(1-(4-Methoxyphenyl)-5-methyl-1H-pyrazol-3-yloxy)ethyl]piperidine
[15] 1-{2-[1-(4-Methoxyphenyl)-5-methyl-1H-pyrazol-3-yloxy]ethyl}-1H-imidazole
[16] 4-{2-[1-(3,4-Dichlorophenyl)-5-phenyl-1H-pyrazol-3-yloxy]ethyl}morpholine
[17] 1-(3,4-Dichlorophenyl)-5-phenyl-3[2-(pyrrolidin-1-yl)ethoxy]-1H-pyrazole
[18] 1-(3,4-Dichlorophenyl)-5-phenyl-3-[3-(pyrrolidin-1-yl)propoxy]-1H-pyrazole
[19] 1-{2-[1-(3,4-Dichlorophenyl)-5-phenyl-1H-pyrazol-3-yloxy]ethyl}piperidine
[20] 1-{2-[1-(3,4-Dichlorophenyl)-5-phenyl-1H-pyrazol-3-yloxy]ethyl}-1H-imidazole
[21] 2-{2-[1-(3,4-dichlorophenyl)-5-phenyl-1H-pyrazol-3-yloxy]ethyl}-1,2,3,4-tetrahydroisoquinoline
[22] 4-{4-[1-(3,4-Dichlorophenyl)-5-methyl-1H-pyrazol-3-yloxy]butyl}morpholine

[23] 1-(3,4-Dichlorophenyl)-5-methyl-3-[4-(pyrrolidin-1-yl)butoxy]-1H-pyrazole
[24] 1-{4-[1-(3,4-Dichlorophenyl)-5-methyl-1H-pyrazol-3-yloxy]butyl}piperidine
[25] 1-{4-[1-(3,4-Dichlorophenyl)-5-methyl-1H-pyrazol-3-yloxy]butyl}-4-methylpiperazine
[26] 1-{4-[1-(3,4-Dichlorophenyl)-5-methyl-1H-pyrazol-3-yloxy]butyl}-1H-imidazole
[27] 4-[1-(3,4-Dichlorophenyl)-5-methyl-1H-pyrazol-3-yloxy]—N,N-diethylbutan-1-amine
[28] 1-{1-(4-[1-(3,4-dichlorophenyl)-5-methyl-1H-pyrazol-3-yloxy]butyl}-4-phenylpiperidine
[29] 1-{1-(4-[1-(3,4-dichlorophenyl)-5-methyl-1H-pyrazol-3-yloxy]butyl}-6,7-dihydro-1H-indol-4(5H)-one
[30] 2-{1-(4-[1-(3,4-dichlorophenyl)-5-methyl-1H-pyrazol-3-yloxy]butyl}-1,2,3,4-tetrahydroisoquinoline
[31] 4-{2-[1-(3,4-dichlorophenyl)-5-isopropyl-1H-pyrazol-3-yloxy]ethyl}morpholine
[32] 2-[1-(3,4-Dichlorophenyl)-5-isopropyl-1H-pyrazol-3-yloxy]—N,N-diethylethanamine
[33] 1-(3,4-Dichlorophenyl)-5-isopropyl-3-[2-(pyrrolidin-1-yl)ethoxy]-1H-pyrazole
[34] 1-(3,4-Dichlorophenyl)-5-isopropyl-3-[3-(pyrrolidin-1-yl)propoxy]-1H-pyrazole
[35] 1-{2-[1-(3,4-Dichlorophenyl)-5-isopropyl-1H-pyrazol-3-yloxy]ethyl}piperidine
[36] 2-{2-[1-(3,4-dichlorophenyl)-5-isopropyl-1H-pyrazol-3-yloxy]ethyl}-1,2,3,4-tetrahydroisoquinoline
[37] 4-{2-[1-(3,4-dichlorophenyl)-1H-pyrazol-3-yloxy]ethyl}morpholine
[38] 2-[1-(3,4-dichlorophenyl)-1H-pyrazol-3-yloxy]N,N-diethylethanamine
[39] 1-(3,4-dichlorophenyl)-3-[2-(pyrrolidin-1-yl)ethoxy]-1H-pyrazole
[40] 1-{2-[1-(3,4-dichlorophenyl)-1H-pyrazol-3-yloxy]ethyl}piperidine
[41] 1-(3,4-dichlorophenyl)-3-[3-(pyrrolidin-1-yl)propoxy]-1H-pyrazole
[42] 1-{2-[1-(3,4-Dichlorophenyl)-5-methyl-1H-pyrazol-3-yloxy]ethyl}piperazine
[43] 1-{2-[1-(3,4-Dichlorophenyl)-5-methyl-1H-pyrazol-3-yloxy]ethyl}pyrrolidin-3-amine
[44] 4-{2-[1-(3,4-Dichlorophenyl)-4,5-dimethyl-1H-pyrazol-3-yloxy]ethyl}morpholine
[45] 4-{2-[1-(3,4-Dichlorophenyl)-4,5-dimethyl-1H-pyrazol-3-yloxy]ethyl}morpholine
[46] 2-[1-(3,4-Dichlorophenyl)-4,5-dimethyl-1H-pyrazol-3-yloxy]—N,N-diethylethanamine
[47] 1-(3,4-Dichlorophenyl)-4,5-dimethyl-3-[2-(pyrrolidin-1-ypethoxy]-1H-pyrazole
[48] 1-(3,4-Dichlorophenyl)-4,5-dimethyl-3-[3-(pyrrolidin-1-yl)propoxy]-1H-pyrazole
[49] 1-{2-[1-(3,4-Dichlorophenyl)-4,5-dimethyl-1H-pyrazol-3-yloxy]ethyl}piperidine
[50] 4-{4-[1-(3,4-dichlorophenyl)-1H-pyrazol-3-yloxy]butyl}morpholine
[51] (2S,6R)-4-{1-(4-[1-(3,4-dichlorophenyl)-1H-pyrazol-3-yloxy]butyl}-2,6-dimethylmorpholine
[52] 1-{4-[1-(3,4-Dichlorophenyl)-1H-pyrazol-3-yloxy]butyl}piperidine
[53] 1-(3,4-Dichlorophenyl)-3-[4-(pyrrolidin-1-yl)butoxy]-1H-pyrazole
[55] 4-[1-(3,4-dichlorophenyl)-1H-pyrazol-3-yloxy]—N,N-diethylbutan-1-amine
[56] N-benzyl-4-[1-(3,4-dichlorophenyl)-1H-pyrazol-3-yloxy]—N-methylbutan-1-amine
[57] 4-[1-(3,4-dichlorophenyl)-1H-pyrazol-3-yloxy]—N-(2-methoxyethyl)-N-methylbutan-1-amine
[58] 4-{4-[1-(3,4-dichlorophenyl)-1H-pyrazol-3-yloxy]butyl}thiomorpholine
[59] 1-[1-(3,4-Dichlorophenyl)-5-methyl-3-(2-morpholinoethoxy)-1H-pyrazol-4-yl]ethanone
[60] 1-{1-(3,4-dichlorophenyl)-5-methyl-342-(pyrrolidin-1-yl)ethoxyl-1H-pyrazol-4-yl}ethanone
[61] 1-{1-(3,4-dichlorophenyl)-5-methyl-3-[2-(piperidin-1-yl)ethoxy]-1H-pyrazol-4-yl}ethanone
[62] 1-{1-(3,4-dichlorophenyl)-3[2-(diethylamino)ethoxy]-5-methyl-1H-pyrazol-4-yl}ethanone
[63] 4-{2[5-Methyl-1-(naphthalen-2-yl)-1H-pyrazol-3-yloxy]ethyl}morpholine
[64] N,N-Diethyl-2-[5-methyl-1-(naphthalen-2-yl)-1H-pyrazol-3-yloxy]ethanamine
[65] 1-{2-[5-Methyl-1-(naphthalen-2-yl)-1H-pyrazol-3-yloxy]ethyl}piperidine
[66] 5-Methyl-1-(naphthalen-2-yl)-3-[2-(pyrrolidin-1-yl)ethoxy]-1H-pyrazole or their pharmaceutically acceptable salts, solvates or a prodrug thereof.

Opioids and opiates are compounds that bind to opioid receptors. Compounds that bind to the opioid receptor within the scope of the present invention include natural opiates, such as morphine, codeine and thebaine; semi-synthetic opiates, derived from the natural opioids, such as hydromorphone, hydrocodone, oxycodone, oxymorphone, desomorphine, diacetylmorphine, nicomorphine, dipropanoylmorphine, benzylmorphine and ethylmorphine; fully synthetic opioids, such as fentanyl, pethidine, methadone, tramadol and propoxyphene; and endogenous opioid peptides, produced naturally in the body, such as endorphins, enkephalins, dynorphins, and endomorphins and their analogues. Preferably, the opioid receptor ligand utilized according to this invention is morphine or its analogues.

The term "analogue" in the context of this invention refers to any entity structurally derived or homologous to a compound that binds to an opioid receptor and ellicit an analgesic effect. Examples of analogues according to this definition, include the morphine analogues disclosed, for instance, in EP0975648 or EP0793364.

The preferred combination of the invention comprises the combination of 4-{2-[5-Methyl-1-(naphthalen-2-yl)-1H-pyrazol-3-yloxy]ethyl}morpholine and morphine.

The combination of the invention may be formulated for its simultaneous separate or sequential administration, with at least a pharmaceutically acceptable carrier, additive, adjuvant or vehicle. This has the implication that the combination of the two active compounds may be administered:

a) As a combination that is being part of the same medicament formulation, the two active compounds being then administered always simultaneously.
b) As a combination of two units, each with one of the active substances giving rise to the possibility of simultaneous, sequential or separate administration. In a particular embodiment, the sigma ligand is independently administered from the opioid or opiate (i.e in two units) but at the same time. In another particular embodiment, the sigma ligand is administered first, and then the opioid or opiate is separately or sequentially administered. In yet another particular embodiment, the opioid or opiate is administered first, and then the sigma ligand is administered, separately or sequentially, as defined.

Each of these particular and different ways of administration produce the desired effect: to potentiate synergistically the opioid or opiate analgesia and/or attenuate its dependence.

The auxiliary materials or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition. The pharmaceutical combination in accordance with the invention can be adapted to any form of administration, be it orally or parenterally, for example pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

Suitable preparations for oral applications are tablets, pills, chewing gums, capsules, granules, drops or syrups.

Suitable preparations for parenteral applications are solutions, suspensions, reconstitutable dry preparations or sprays.

The combination of the invention may be formulated as deposits in dissolved form or in patches, for percutaneous application.

Skin applications include ointments, gels, creams, lotions, suspensions or emulsions.

The preferred form of rectal application is by means of suppositories.

The combination of at least one opioid or opiate and at least one compound of general formula I are suited for use in potentiating the analgesic effect of opioids or opiates and/or for decreasing their dependency. These combinations could be administered simultaneously, separately or sequentially.

The combination of the invention shows both the effect of potentiating the analgesia produced by opioids or opiates and for decreasing their dependency but could be used; in any case, to achieve solely one of these objectives.

For example, for the co-administration of a compound of formula (I) and an opioid or opiate could be directed only to maximize the opioid or opiate analgesic effect. Under this scenario, it will be possible to attain the added benefit of maintaining the same analgesic level while reducing the opioid or opiate dosage.

In another embodiment, the administration may be intended just for the attenuation of the dependency or addiction induced by opioids or opiates.

In a preferred embodiment, the invention comprises the use of a combination se defined herein for both potentiating the analgesic effect of opioids or opiates and decreasing at the same time the dependency induced by them.

The dosage regime that must be administered to the patient depends on the patient's weight, the type of application, the condition and severity of the disease. A preferred dosage regime of comprises an administration of a compound of formula (I) within a range of 0.5 to 100 mg/kg and of the opioid or opiate from 0.15 to 15 mg/kg and it is administered daily in one or several doses.

Another object of the invention is based on the discovery that sigma ligands are capable at the same time of synergistically enhancing the analgesic effect of opioids and opiates and decreasing the dependence induced by them. This aspect of the invention comprises a combination of at least one sigma ligand and at least an opioid or opiate compound. The combination is then administered in a simultaneous, separate or sequential manner to potentiate the analgesic effect of the opioid or opiate and decrease its dependency.

In another embodiment of the present invention, the opiate used is preferably morphine or analogues thereof.

The following examples will serve to illustrate the invention.

EXAMPLE 1

Synergistic Effect of Compound 63 in Analgesia Mediated by Morphine a) Modulation of Morphine Analgesia in the Tail Flick Test The analgesia induced by the combination of compound 63, a sigma-1 ligand, and morphine was assessed by the tail flick test following the method described by Carlsson et al [Neurosci Lett. 1986 Nov. 21; 71(3):356-60] in CD-1 wild type (WT) mice as well as in sigma-1 deficient mice (KO).

First, the efficacy of compound 63 alone was evaluated in WT as well as KO mice by its administration at different doses (10, 20, 40 and 80 mg/kg, i.p.). Compound 63 had no significant effect on response latency except for the highest dose tested. As expected, this effect was even no present for KO mice (see FIG. 1).

Figure 2:
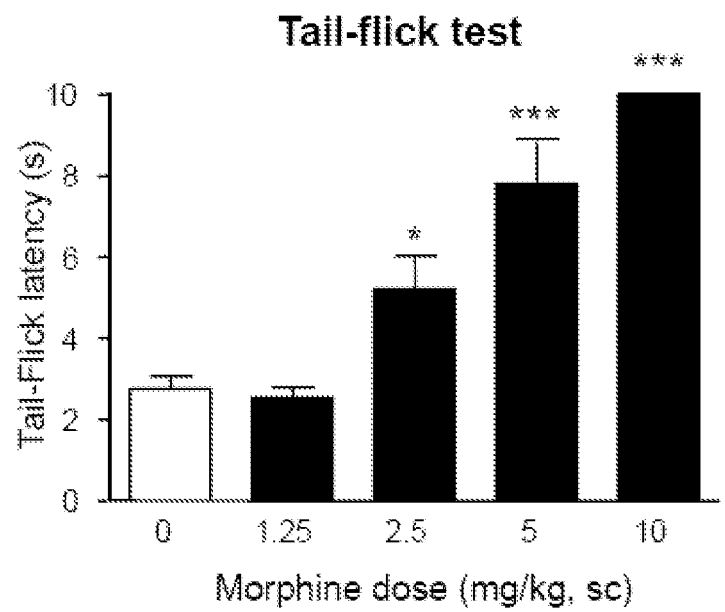
FIG. 2: Dose-response effects of acute administration of morphine (1.25, 2.5, 5 and 10 mg/kg, sc) in the tail-flick test in male CD-1 WT mice. Compounds were injected 30 min before the test. Data, obtained from 8 animals per group, are presented as the mean±SEM of the tail-flick latency (s). *$p<0.05$, ***$p<0.001$ vs. vehicle (saline) treated group (Newman-Keuls Multiple comparison Test post-ANOVA).
Figure 3:
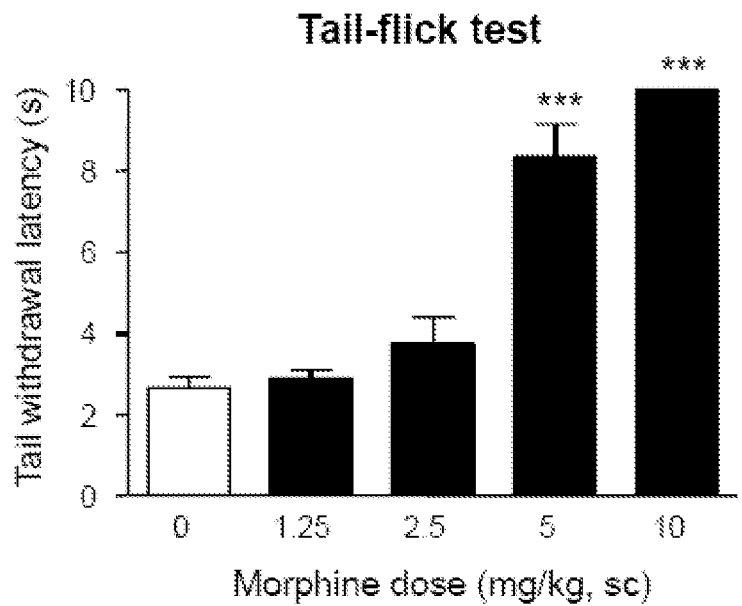
FIG. 3: Dose-response effects of acute administration of morphine (1.25, 2.5, 5 and 10 mg/kg, sc) in the tail-flick test in male CD-1 σR-KO mice. Compounds were injected 30 min before the test. Data, obtained from 10 to 11 animals per group, are presented as the mean±SEM of the tail-flick latency (s). ***$p<0.001$ vs. vehicle (saline) treated group (Newman-Keuls Multiple comparison Test post-ANOVA).
Figure 4:
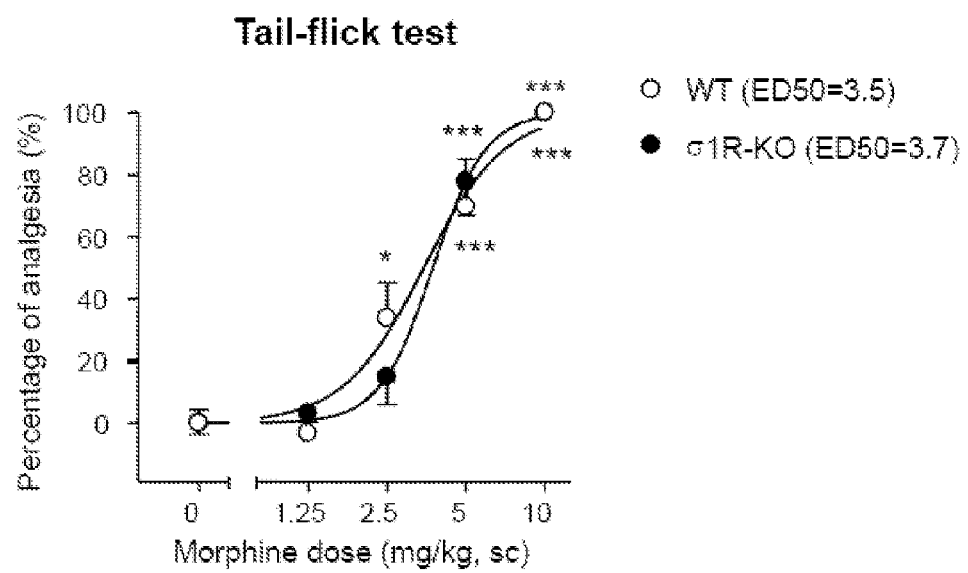
FIG. 4: Sigmoidal dose-response curves of morphine (1.25, 2.5, 5 and 10 mg/kg, sc) in the tail-flick test in male CD-1 WT and al R-KO mice. Compounds were injected 30 min before the test. Data, obtained from 8 to 11 animals per group, are presented as the mean±SEM percentages of analgesia (%). Insert: Tail-Flick latency of both, WT and σ1R-KO, vehicle treated groups. *$p<0.05$, ***$p<0.001$ vs. corresponding vehicle group (saline) (Newman-Keuls Multiple comparison Test post-ANOVA).

In contrast morphine produced a clear dose-dependent analgesic effect either in WT and KO mice with similar efficacy and potency (ED 50 3.5 and 3.7 mg/kg for WT and KO, respectively) indicating that KO mice perceive normally the morphine analgesia in these conditions of tail flick assay (see FIGS. 2, 3 and 4).

Figure 5:
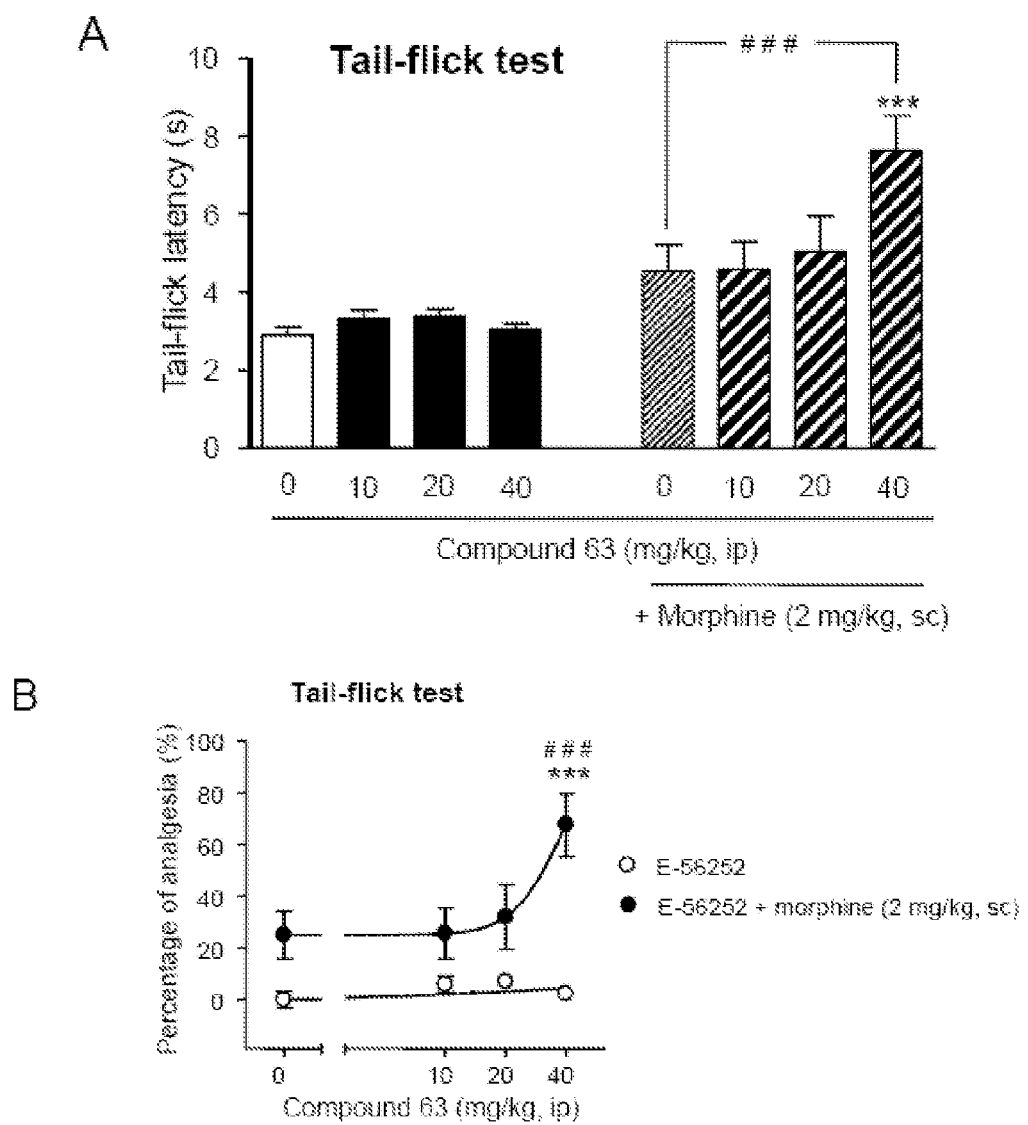
FIG. 5: A) Potentiation of the antinociceptive actions of morphine (2 mg/kg, sc) by compound 63 (10, 20, 40 mg/kg, ip) in the tail-flick test in male CD-1 WT mice. Compounds were injected 30 min before the test. Data, obtained from 11 to 12 animals per group, are presented as the mean±SEM of the tail-flick latency (s). ***$p<0.001$ vs. vehicle treated group; ###$p<0.001$ vs. morphine (2 mg/kg) group (Newman-Keuls Multiple comparison Test post-ANOVA). B) Sigmoidal dose-response curves representation.

Next, the analgesia produced by the combination of compound 63 and morphine was evaluated in WT mice. FIG. 5 shows the potentiation of the antinociceptive action of morphine (2 mg/kg, s.c.) by compound 63 represented by the tail flick latency (A) and by the percentage of analgesia (B).

Figure 6:
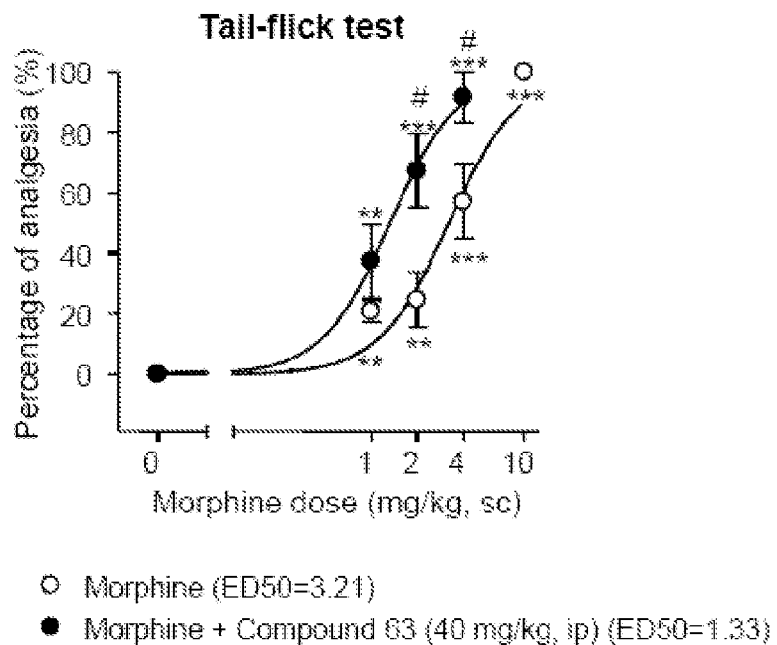
FIG. 6: Sigmoidal dose-response curves of morphine (1, 2, 4, and 10 mg/kg, sc) and combination of compound 63 (40 mg/kg, ip) with morphine (1, 2 and 4 mg/kg, sc) in the tail-flick test in male CD-1 WT mice. Compounds were injected 30 min before the test. Data, obtained from 10 to 11 animals per group, are presented as the mean±SEM percentages of analgesia (%). $p<0.01$; *$p<0.001$ vs. corresponding vehicle treated group (Newman-Keuls Multiple comparison Test post-ANOVA).; #$p<0.05$ vs. corresponding group treated with morphine (2 and 4 mg/kg) (Unpaired t-test).

As shown in FIG. 6, the sigmoidal dose response curves in CD1 WT mice of the combination of morphine (1, 2 and 4 mg/kg, s.c.) with compound 63 (40mg/kg, i.p.) when compared to morphine alone (1, 2, 4 and 10 mg/kg, s.c.) shows a significant increase in the percentage of analgesia of the combination and a significant decrease in the ED50 of the combination (ED50=1.33) vs morphine alone (ED50=3.21). The combination of morphine with 40 mg/kg of compound 63 increases the analgesia potency of morphine alone by a factor of 2.4.

Figure 7:
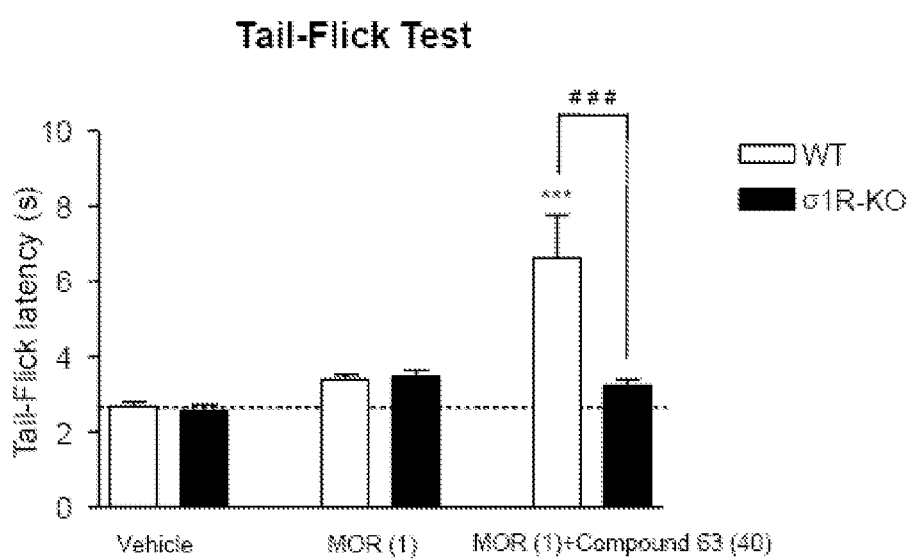
FIG. 7: Antinociceptive effect of morphine (MOR) and the combination of morphine +compound 63 in the tail-flick test in WT and σ1R-KO male CD-1 mice. Compounds were injected intraperitoneally 30 min before the test. Dose of drugs are expressed in mg/kg (brackets in the graph). Data, obtained from 6 to 14 animals per group, are presented as the mean±SEM of the tail-flick latency (s). ***$p<0.001$ vs. vehicle treated WT group; ###$p<0.001$ vs. MOR+compound 63 treated WT group. (Newman-Keuls Multiple comparison Test post-ANOVA).

Groups of mice received morphine alone (1 mg/kg) and in combination with compound 63 (40 mg/kg) and it was found only 10% of analgesia with morphine alone (no significant) and 55% of analgesia with the combination. This synergistic effect is, however, abolished when the combination is administered to sigma-1 KO mice as shown in FIG. 7.

b) Modulation of Morphine Analgesia in the Hot Plate Test

In order to further study the effect of compound 63 on morphine analgesia, experiments were performed in the hot-plate (supraspinally integrated responses) as described by Janicki et al [Pharmacol Biochem Behave.1979 Apr; 10(4):623-6]. The effect of compound 63 on morphine analgesia was examined: groups of mice received morphine alone (2.5 mg/kg) and in combination with compound 63 (40 mg/kg). When the hot-plate test is performed at 50° C., we found a 45% of analgesic activity with morphine alone, and 83% with the morphine and compound 63 combination. When it is performed at 55° C., morphine produced 43% of analgesic activity and the combination 94%. Therefore, compound is able to enhance morphine analgesia also in the hot-plate test.

EXAMPLE 2

Enhanced Synergistic Effect of Compound 63 and 11 in Analgesia Mediated by Morphine when Compared to Well Known Sigma Ligand BD1063

The analgesic effect of two of the compounds of the invention (compound 63 and compound 11) and of BD1063 well known sigma-1 ligand in combination with morphine was evaluated in CD-1 wild type (WT) mice by the tail flick test as under example 1. Compound 63 and 11 and BD1063 where administered in a single dose of 40 mg/kg i.p 30 minutes before the administration of morphine (1 mg/kg s.c.)

Figure 8:
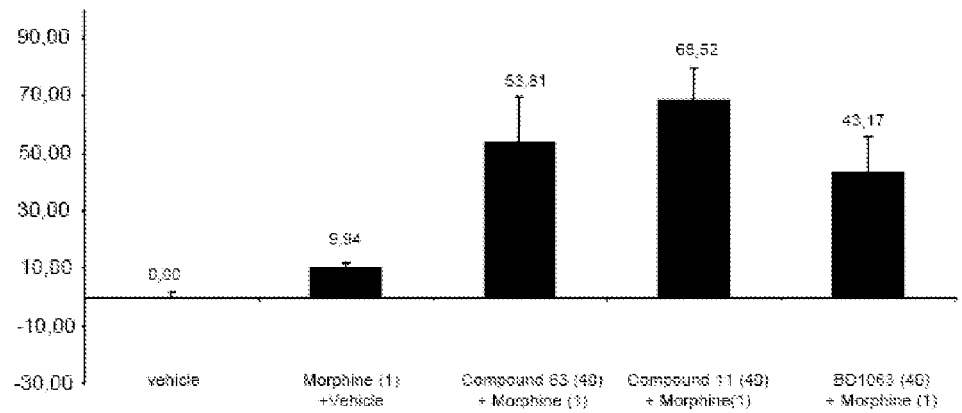
FIG. 8: Enhanced synergistic effect of compound 63 and 11 in analgesia mediated by morphine when compared to well known sigma ligand BD1063.

The results shown in FIGS. 8 demonstrate that all combination of sigma ligand with morphine produced an enhancement of the analgesic effect of morphine although this effect was more pronounced in the case of the co administration with the compound 63 and 11 of the present invention.

EXAMPLE 3

Attenuation of Dependence Induced by Morphine By Co-Administration with Compound 63

The attenuation of the addictive effect of morphine by compound 63 was tested with the place conditioning paradigm model. The place conditioning paradigm is a behavioural model used in mice to evaluate the possible rewarding/aversive properties of a drug. In this paradigm the rewarding effects of the drug are associated with the physical characteristics of an environment, and thus, mice will prefer spend more time in the environment associated with a drug having rewarding properties. This model also allows exploring the aversive effects of a drug, and in this case, the mouse will avoid stay in the compartment associated with the drug having aversive properties.

The purpose was to evaluate the effects induced by the administration compound 63 in the mouse place conditioning paradigm and their capability to modify the rewarding properties of morphine in this paradigm. Two different doses of morphine were tested and compound 63 was administered at a single dose calculated from the data previously obtained in the neuropathic pain model (data not shown).

Male CD-1 mice (Charles River, France) weighing 20-22 gr at the beginning of the experiment were used. Mice were identified by a mark on the tail and housed individually in controlled laboratory conditions with the temperature maintained at 21±1 ° C., humidity at 55±10%, and light controlled cycle (light on at 08:00 h; light off at 20:00 h). All experiments were conducted in a sound attenuated room. The mice were given access to food and water ad libitum except during the behavioural testing. All experimental procedures and animal husbandry were conducted according to standard ethical guidelines (European Community Guidelines on the Care and Use of Laboratory Animals) and approved by the local ethical committee.

The following experimental groups were tested:
Group 1 (n=12): saline+saline
Group 2 (n=14): morphine (1.5 mg/kg s.c.)+saline
Group 3 (n=11): morphine (5 mg/kg s.c.)+saline
Group 4 (n=12): saline+compound 63 (25 mg/kg s.c.)
Group 5 (n=11): morphine (1.5 mg/kg s.c.)+compound 63 (25 mg/kg s.c.)
Group 6 (n=12): morphine (5 mg/kg s.c.)+compound 63 (25 mg/kg s.c.)

The rewarding properties of morphine and the possible rewarding/aversive effect of compound 63 were evaluated by using an apparatus adapted for the conditioning place preference paradigm. The apparatus consists of two main square conditioning compartments separated by a triangular central division. During the preconditioning phase, each mouse was placed in the middle of the central division and had free access to both compartments of the conditioning apparatus for 18 min, with the time spent in each compartment recorded. Treatments were counterbalanced between compartments in order to use an unbiased procedure. For conditioning phase, mice were treated during 6 days with alternate injections of drugs (morphine and/or compound 63) or saline. Saline and compound 63 were administered 30 min before morphine or saline injection. Mice were confined into the corresponding compartment immediately after morphine or saline administration by using guillotine doors matching walls for 20 min. Drugs were administered on days 1, 3 and 5, and saline on days 2, 4 and 6. Control animals received saline every day. The test phase was conducted as in the preconditioning phase, i.e. free access to both compartments for 18 min, and the time spent in each compartment was recorded. A score was calculated for each mouse as the difference between the post-conditioning and pre-conditioning time spent in the drug-paired compartment. Data were expressed as raw time score values (seconds) (FIG. 9) and time spent in the drug-paired compartment during pre-conditioning and test phases (seconds) (FIG. 10). Time score values were compared using one-way ANOVA (between subjects) followed by a Dunnet post-hoc comparison. Values of the time spent for each group of mice in drug-paired compartment during the pre-conditioning and post-conditioning measurements were compared by using a two-tailed Student's paired t-test.

Figure 9:
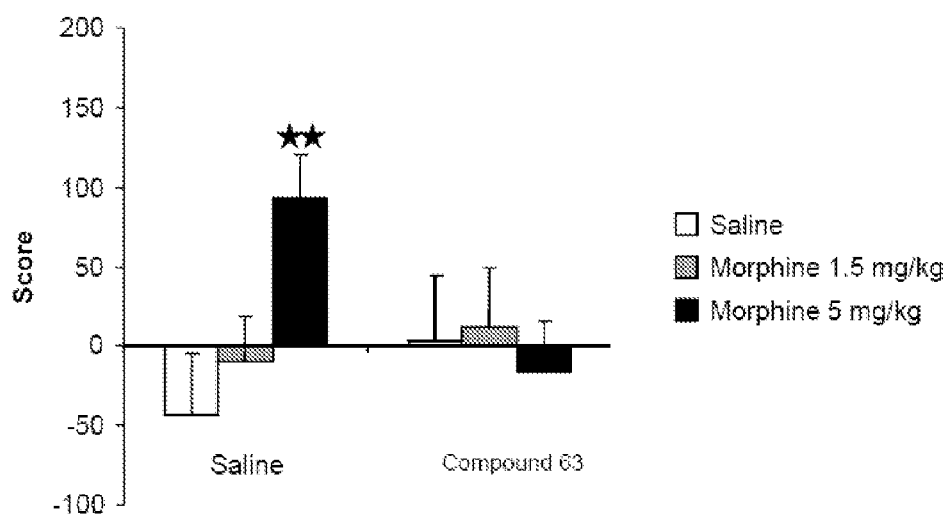
FIG. 9: Effect of compound 63 (25 mg/kg s.c) on the rewarding effects induced by morphine in the place conditioning paradigm (score values).
Figure 10:
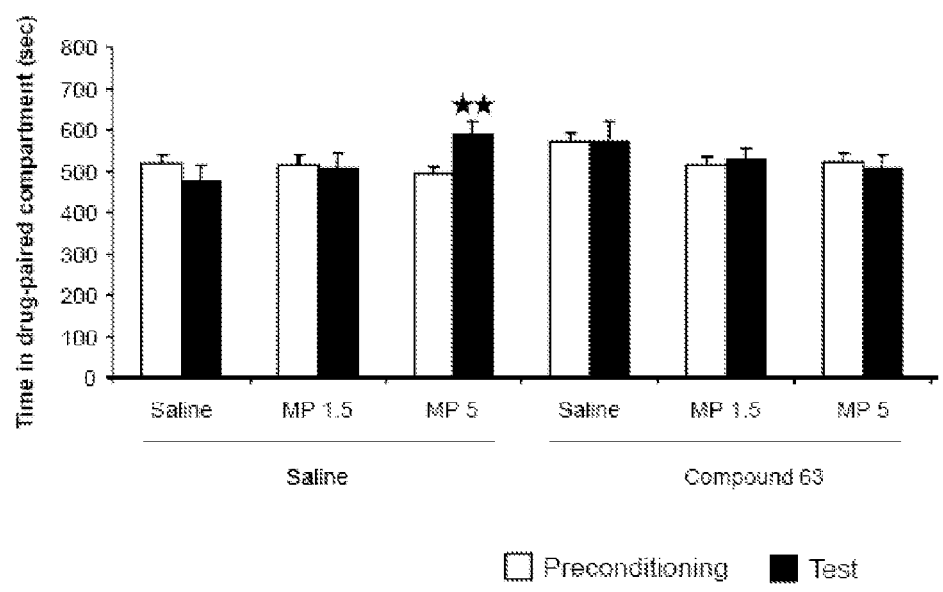
FIG. 10: Effect of compound 63 (25mg/kg s.c.) on the rewarding effects induced by morphine in the place conditioning paradigm. Time spent in the drug paired compartment during the preconditioning and test phase.

The results as shown in FIGS. 9 and 10 give rise to the following conclusions:
Morphine administered at the dose of 5 mg/kg induced rewarding effects revealed by a conditioned place preference: No effects were observed when morphine was administered at the dose of 1.5 mg/kg. These effective and non-effective doses of morphine were used to evaluate the possible interactions with compound 63.
Compound 63 (25 mg/kg) did not produce any place conditioning effect when administered alone. This result suggests that compound 63 does not produce rewarding or aversive effects when administered at this dose.
Compound 63 (25 mg/kg) attenuated the rewarding effects induced by morphine in the place conditioning paradigm. Thus, compound 63 suppressed the rewarding responses produced by the effective dose of morphine (5 mg/kg) and did not produce any conditioned response when it was associated to the non-effective dose of morphine (1.5 mg/kg).

The invention claimed is:

1. A combination for simultaneous, separate or sequential administration comprising:
   a) at least one sigma ligand selected from the group consisting of 4-{2-[1-(4-methoxyphenyl)-5-methyl-1H-pyrazol-3-yloxy]ethyl}morpholine, 4-{2-[5-Methyl-1-(naphthalene-2-yl)-1H-pyrazol-3-yloxy]ethyl}morpholine and pharmaceutically acceptable salts, isomers and solvates thereof; and b) at least one opioid or opiate compound selected from morphine or a structural derivative thereof, fentanyl or tramadol.

2. The combination of claim 1 wherein the opiate is selected from the group consisting of morphine, hydromorphone, oxymorphone, desomorphine, diacetylmorphine, nicomorphine, dipropanoylmorphine, benzylmorphine, ethylmorphine, codeine, oxycodone, fentanyl and tramadol.

3. The combination of claim 1 wherein the combination comprises: a) 4-{2-[1-(4-methoxyphenyl)-5-methyl-1H-pyrazol-3-yloxy]ethyl}morpholine or a pharmaceutically acceptable salt, isomer or solvate thereof and b) at least one opioid or opiate compound selected from morphine, codeine, oxycodone, fentanyl and tramadol.

4. The combination of claim 1 wherein the combination comprises:
   a) 4-{2-[5-methyl-1-(naphthalen-2-yl)-1H-pyrazol-3-yloxy]ethyl}morpholine or a pharmaceutically acceptable salt, isomer or solvate thereof and b) at least one opioid or opiate compound selected from morphine, codeine, oxycodone, fentanyl and tramadol.

5. A method for potentiating the analgesic effect of morphine or a structural derivative thereof, fentanyl and tramadol and/or for decreasing the dependency induced thereby, comprising administering to a patient in need thereof, a therapeutically effective amount of a combination for simultaneous, separate or sequential administration comprising:
   a) at least one sigma ligand selected from the group consisting of 4-{2-[1-(4-methoxyphenyl)-5-methyl-1H-pyrazol-3-yloxy]ethyl }morpholine, 4-{2-[5-Methyl-1-(naphthalen-2-yl)-1H-pyrazol-3-yloxy]ethyl}morpholine and pharmaceutically acceptable salts, isomers and solvates thereof; and
   b) at least one opioid or opiate compound selected from morphine or a structural derivative thereof, fentanyl or tramadol.

6. The method of claim 5 for potentiating the analgesic effect of morphine or a structural derivative thereof, fentanyl and tramadol.

7. The method of claim 5 for decreasing the dependency induced by morphine or a structural derivative thereof, fentanyl and tramadol.

8. The method of claim 5 wherein the opiate is selected from the group consisting of morphine, hydromorphone, oxymorphone, desomorphine, diacetylmorphine, nicomorphine, dipropanoylmorphine, benzylmorphine, ethylmorphine, codeine, oxycodone, fentanyl and tramadol.

9. The method of claim 5 wherein the combination comprises: a) 4-{2-[1-(4-methoxyphenyl)-5-methyl-1H-pyrazol-3-ylox]ethyl}morpholine or a pharmaceutically acceptable salt, isomer or solvate thereof and b) at least one opioid or opiate compound selected from morphine, codeine, oxycodone, fentanyl and tramadol.

10. The method of claim 5 wherein the combination comprises: a) 4-{2-[5-methyl-1-(naphthalen-2-yl)-1H-pyrazol-3-yloxy]ethyl}morpholine or a pharmaceutically acceptable salt, isomer or solvate thereof and b) at least one opioid or opiate compound selected from morphine, codeine, oxycodone, fentanyl and tramadol.

* * * * *